United States Patent
Sando et al.

(10) Patent No.: US 10,619,161 B2
(45) Date of Patent: Apr. 14, 2020

(54) APTAMER CAPABLE OF BINDING TO HGF RECEPTOR

(71) Applicant: The University of Tokyo, Tokyo (JP)

(72) Inventors: Shinsuke Sando, Tokyo (JP); Ryosuke Ueki, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 248 days.

(21) Appl. No.: 15/508,973

(22) PCT Filed: Sep. 9, 2015

(86) PCT No.: PCT/JP2015/075581
§ 371 (c)(1),
(2) Date: Mar. 6, 2017

(87) PCT Pub. No.: WO2016/039371
PCT Pub. Date: Mar. 17, 2016

(65) Prior Publication Data
US 2017/0275630 A1    Sep. 28, 2017

Related U.S. Application Data

(60) Provisional application No. 62/047,747, filed on Sep. 9, 2014.

(51) Int. Cl.
*C12N 15/115* (2010.01)
*C12N 5/00* (2006.01)

(52) U.S. Cl.
CPC .......... *C12N 15/115* (2013.01); *C12N 5/0018* (2013.01); *C12N 2310/151* (2013.01); *C12N 2310/16* (2013.01); *C12N 2310/51* (2013.01); *C12N 2310/531* (2013.01); *C12N 2501/12* (2013.01)

(58) Field of Classification Search
None
See application file for complete search history.

(56) References Cited

U.S. PATENT DOCUMENTS

2013/0129718 A1    5/2013    Wong et al.

FOREIGN PATENT DOCUMENTS

WO    2012/076190 A1    6/2012

OTHER PUBLICATIONS

Trusolino et al., Scatter-Factor and Semaphorin Receptors: Cell Signalling for Invasive Growth, Nature Reviews Cancer, vol. 2, Apr. 2002, pp. 289-300 (12 pages), cited in the specification.
Ueki et al., DNA aptamers for receptor signaling inhibition, Program Abst. Int. Symp. Nucleic Acids Chem., 2013, vol. 40, pp. 252-253 (2 pages), cited in ISR.
Ueki et al., Control of receptor activity by synthetic molecules (2): Approaches for affinity improvement of DNA aptamer, Dai 95 Kai Annual Meeting of the Chemical Society of Japan in Spring (2015) Koen Yokoshu, Mar. 11, 2015, 2 J5-13 (1 page), cited in ISR.
Kanda et al., Control of receptor activity by synthetic molecules (1): Efforts toward efficient receptor activation by DNA aptamer, Dai 95 Kai Annual Meeting of the Chemical Society of Japan in Spring (2015) Koen Yokoshu, Mar. 11, 2015, 2 J5-12 (1 page), cited in ISR.
International Search Report dated Nov. 10, 2015, issued in counterpart International Application No. PCT/JP2015/075581 (2 pages).

*Primary Examiner* — James D Schultz
(74) *Attorney, Agent, or Firm* — Westerman, Hattori, Daniels & Adrian

(57) ABSTRACT

Provided is an aptamer including a polynucleotide of any of the following (a) to (c) and capable of binding to an HGF receptor to exhibit an activity of inhibiting the binding of HGF to the HGF receptor. (a) A polynucleotide consisting of a base sequence set forth in SEQ ID NO:1, (b) A polynucleotide consisting of a base sequence having the deletion, substitution, insertion and/or addition of one to several bases in the base sequence set forth in SEQ ID NO:1, and (c) A polynucleotide consisting of a base sequence having a sequence identity of 80% or more to the base sequence set forth in SEQ ID NO:1.

9 Claims, 12 Drawing Sheets

Specification includes a Sequence Listing.

Aptamer
(5'-FITC)

Western blotting

SL1_dimer5

SEQUENCE LISTING

```
<160> NUMBER OF SEQ ID NOS: 11

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: G-loop

<400> SEQUENCE: 1
ggatggtagc tcggtcgggg tgggtgggtt gg                                    32

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: 3T

<400> SEQUENCE: 2
ggttggtagc tcggtcgggg tgggtgggtt gg                                    32

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: 29A

<400> SEQUENCE: 3
ggatggtagc tcggtcgggg tgggtgggat gg                                    32

<210> SEQ ID NO 4
```

```
<211> LENGTH: 32
<212> TYPE: DNA
<213> ORGANISM: Artificial Sequence
<220> FEATURE:
<223> OTHER INFORMATION: Description of Artificial Sequence: 3T29A

<400> SEQUENCE: 4
ggttggtagc tcggtcgggg tgggtgggat gg                                   32

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence: SL1

<400> SEQUENCE: 5
atcaggctgg atggtagctc ggtcggggtg ggtgggttgg caagtctgat                50

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: SL1 reverse
      sequence

<400> SEQUENCE: 6
tagtctgaac ggttgggtgg gtggggctgg ctcgatggta ggtcggacta                50

<210> SEQ ID NO 7
<211> LENGTH: 71
<212> TYPE: DNA
<213> ORGANISM: Artificial Sequence
<220> FEATURE:
<223> OTHER INFORMATION: Description of Artificial Sequence: SL1_A

<400> SEQUENCE: 7
cgatcagtct agcatccatc tatcaggctg gatggtagct cggtcggggt gggtgggttg     60
gcaagtctga t                                                          71

<210> SEQ ID NO 8
<211> LENGTH: 71
<212> TYPE: DNA
<213> ORGANISM: Artificial Sequence
<220> FEATURE:
<223> OTHER INFORMATION: Description of Artificial Sequence: SL1_B

<400> SEQUENCE: 8
gatggatgct agactgatcg tatcaggctg gatggtagct cggtcggggt gggtgggttg     60
gcaagtctga t                                                          71

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Comp_A

<400> SEQUENCE: 9
gatggatgct agactgatcg                                                 20

<210> SEQ ID NO 10
<211> LENGTH: 20
<212> TYPE: DNA
```

```
<213> ORGANISM: Artificial Sequence
<220> FEATURE:
<223> OTHER INFORMATION: Description of Artificial Sequence: Comp_B

<400> SEQUENCE: 10
cgatcagtct agcatccatc                                                    20

<210> SEQ ID NO 11
<211> LENGTH: 105
<212> TYPE: DNA
<213> ORGANISM: Artificial Sequence
<220> FEATURE:
<223> OTHER INFORMATION: Description of Artificial Sequence: SL1_dimer_5

<400> SEQUENCE: 11
atcaggctgg atggtagctc ggtcggggtg ggtgggttgg caagtctgat tttttcgtgt         60
cacggatggt agctcggtcg gggtgggtgg gttggcagtg acacg                        105
```

APTAMER CAPABLE OF BINDING TO HGF RECEPTOR

Priority is claimed on U.S. Provisional Application No. 62/047,747, filed on Sep. 9, 2014, the content of which is incorporated herein by reference.

TECHNICAL FIELD

The present invention relates to an aptamer, an agent for treating or preventing an HGF receptor signaling-related disease, an agent for inhibiting metastasis of a cancer cell, a cell culture composition, a cell culture method, a binding inhibition method, a method for inhibiting differentiation of a cell, a method for inhibiting growth of a cell, a method for inhibiting migration of a cell, a method for activating an HGF receptor, a method for inducing differentiation of a cell, a method for promoting growth of a cell, and a method for promoting migration of a cell.

BACKGROUND ART

With regard to receptor signaling, it is known that when a cell receives a ligand at the receptor on the cell membrane, a signal is transmitted into the cell, whereby differentiation and growth of the cell are controlled. By the acceptance of a signaling molecule, the cell is capable of recognizing the surrounding environment and situation.

c-Met is a tyrosine kinase HGF receptor, and a hepatocyte growth factor (HGF) is a ligand of c-Met. When HGF binds to c-Met, a dimer of c-Met is formed, a c-Met intracellular domain is phosphorylated, and therefore intracellular signaling is initiated. The binding of c-Met to HGF leads to activation of c-Met.

The activation of c-Met is known to result in growth and differentiation induction of hepatocytes. In addition, it has been pointed out that abnormal enhancement of c-Met signaling is involved in the metastasis of cancer cells (Non-Patent Document 1). Accordingly, there has been a need for a molecular tool capable of controlling the c-Met activity.

CITATION LIST

Non-Patent Literature

[Non-Patent Document 1] L. Trusolino et al., Nat Rev. Cancer., 2, pp 289 to 300 (2002)

SUMMARY OF INVENTION

Technical Problem

HGF is produced as a molecule that binds to an HGF receptor. However, in production of HGF, it is generally essential to use an expression system, and HGF to be provided becomes expensive. In addition, an HGF protein suffers from a problem that the quality control is complicated.

The present invention has been made in view of the above circumstances, and an object thereof is to provide an aptamer capable of binding to an HGF receptor.

Solution to Problem

One embodiment of the present invention is to provide the following (1) to (20).

(1) An aptamer comprising a polynucleotide of any of the following (a) to (c) and capable of binding to an HGF receptor to exhibit an activity of inhibiting the binding of HGF to the HGF receptor,
(a) a polynucleotide consisting of a base sequence set forth in SEQ ID NO: 1,
(b) a polynucleotide consisting of a base sequence having the deletion, substitution, insertion and/or addition of one to several bases in the base sequence set forth in SEQ ID NO: 1, and
(c) a polynucleotide consisting of a base sequence having a sequence identity of 80% or more to the base sequence set forth in SEQ ID NO: 1.
(2) The aptamer according to (1), which has a loop structure at least a part of which is formed of the polynucleotide of any of (a) to (c).
(3) The aptamer according to (2), which has a stem structure consisting of a double-stranded polynucleotide connected to the loop structure.
(4) The aptamer according to (2) or (3), in which the loop structure consists of a polynucleotide chain having 28 to 40 bases.
(5) The aptamer according to any one of (1) to (4), in which the polynucleotide of (a) to (c) forms a guanine quadruplex structure.
(6) An aptamer having a multi-structure in which two or more polynucleotides of any of the following (a) to (c) are connected and capable of binding to an HGF receptor to exhibit an activity of activating the HGF receptor,
(a) a polynucleotide consisting of a base sequence set forth in SEQ ID NO: 1,
(b) a polynucleotide consisting of a base sequence having the deletion, substitution, insertion and/or addition of one to several bases in the base sequence set forth in SEQ ID NO: 1, and
(c) a polynucleotide consisting of a base sequence having a sequence identity of 80% or more to the base sequence set forth in SEQ ID NO: 1.
(7) The aptamer according to (6), which has a multi-loop structure in which two or more loop structures at least a part of which is formed of the polynucleotide of any of (a) to (c) are connected.
(8) The aptamer according to (6) or (7), in which two or more polynucleotides of (a) to (c) are connected by a linker, and the length of the linker is 80 bases or less in terms of polynucleotide.
(9) An agent for treating or preventing an HGF receptor signaling-related disease, comprising the aptamer according to any one of (1) to (8) as an active ingredient.
(10) An agent for inhibiting metastasis of a cancer cell, comprising the aptamer according to any one of (6) to (8) as an active ingredient.
(11) A cell culture composition, comprising the aptamer according to any one of (1) to (8) as an active ingredient.
(12) A cell culture method, comprising culturing an HGF receptor-expressing cell in a medium containing the aptamer according to any one of (1) to (8).
(13) A method for inhibiting the binding of HGF to an HGF receptor, comprising bringing the aptamer according to any one of (1) to (5) into contact with an HGF receptor-expressing cell.
(14) A method for inhibiting differentiation of a cell, comprising bringing the aptamer according to any one of (1) to (5) into contact with an HGF receptor-expressing cell.
(15) A method for inhibiting growth of a cell, comprising bringing the aptamer according to any one of (1) to (5) into contact with an HGF receptor-expressing cell.

(16) A method for inhibiting migration of a cell, comprising bringing the aptamer according to any one of (1) to (5) into contact with an HGF receptor-expressing cell.

(17) A method for activating an HGF receptor, comprising bringing the aptamer according to any one of (6) to (8) into contact with an HGF receptor-expressing cell.

(18) A method for inducing differentiation of a cell, comprising bringing the aptamer according to any one of (6) to (8) into contact with an HGF receptor-expressing cell.

(19) A method for promoting growth of a cell, comprising bringing the aptamer according to any one of (6) to (8) into contact with an HGF receptor-expressing cell.

(20) A method for promoting migration of a cell, comprising bringing the aptamer according to any one of (6) to (8) into contact with an HGF receptor-expressing cell.

DESCRIPTION OF EMBODIMENTS

«Aptamer»

The aptamer of one embodiment of the present invention has a polynucleotide of any of the following (a) to (c) and binds to an HGF receptor to exhibit an activity of inhibiting the binding of HGF to the HGF receptor.

(a) A polynucleotide consisting of a base sequence set forth in SEQ ID NO: 1, (b) A polynucleotide consisting of a base sequence having the deletion, substitution, insertion and/or addition of one to several bases in the base sequence set forth in SEQ ID NO: 1, and (c) A polynucleotide consisting of a base sequence having a sequence identity of 80% or more to the base sequence set forth in SEQ ID NO: 1.

The term "aptamer" refers to a molecule capable of binding to a target molecule, and there are known a nucleic acid and a peptide as examples thereof. The aptamer of the present embodiment is a nucleic acid aptamer which binds to an HGF receptor.

In the present specification, the nucleic acid may be a natural nucleic acid such as DNA or RNA or may be an artificial nucleic acid such as a locked nucleic acid (LNA) or bridged nucleic acid (BNA). The nucleic acid may be a nucleic acid analogue represented by a peptide nucleic acid such as a Peptide Nucleic Acid (PNA) as long as it has a function equivalent to that of the nucleic acid. The nucleic acid constituting an aptamer may be a combination of a plurality of kinds of nucleic acids such as a combination of DNA and LNA.

The HGF receptor is a protein capable of binding to HGF, and as the HGF receptor, there is known c-Met which is a kind of receptor tyrosine kinase. The receptor tyrosine kinase is known as a transmembrane protein, has a ligand-binding domain on the extracellular side, and has an intracellular domain on the cytoplasmic side. The ligand-binding domain is capable of binding to a ligand. The intracellular domain has a kinase activity.

The receptor tyrosine kinase is known to form a dimer by the binding of the ligand thereto. When the dimer is formed, tyrosine residues in the intracellular domain of the dimer are phosphorylated with each other. The HGF receptor to which the aptamer of the present embodiment binds may be a monomer, a dimer or higher order complex.

Examples of the HGF receptor-expressing cells include hepatocytes, epithelial cells, keratinocytes, nerve cells, and myocardial cells.

Figure 1:
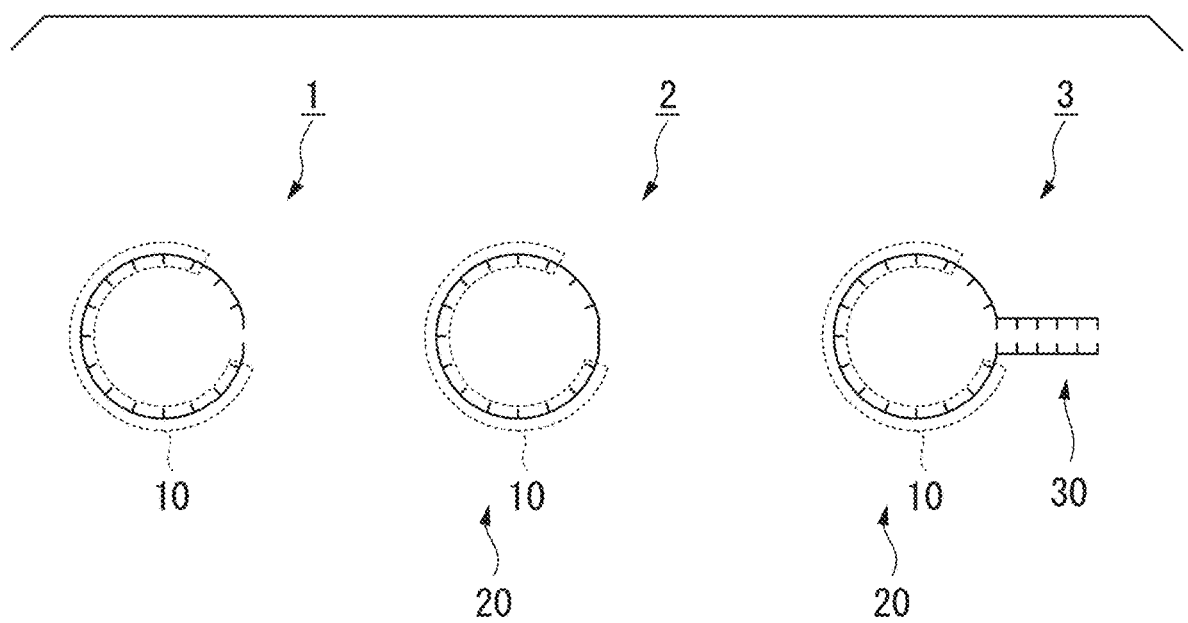
FIG. 1 is a schematic diagram of an aptamer in one embodiment.

FIG. 1 shows a schematic diagram of an aptamer according to one embodiment. An aptamer 1 consists of a polynucleotide and has a polynucleotide 10 of any of the above (a) to (c).

As will be described in Examples to be given hereinafter, the present inventors have found that a nucleic acid having (a) a polynucleotide consisting of a base sequence set forth in SEQ ID NO: 1 has an ability to bind to an HGF receptor.

Thus, the aptamer according to one embodiment is an aptamer having the following polynucleotide of (a). (a) A polynucleotide consisting of a base sequence set forth in SEQ ID NO: 1.

Generally, a polynucleotide with the deletion, substitution, insertion and/or addition of one to several bases in the polynucleotide is also known to have the same function as the original polynucleotide. Further, as will be described in Examples to be given hereinafter, the present inventors have found that a nucleic acid having a polynucleotide in which the base sequence of the polynucleotide of (a) has been partially modified also has an ability to bind to an HGF receptor, similar to the polynucleotide of (a).

Thus, the aptamer according to one embodiment is an aptamer having the following polynucleotide of (b). (b) A polynucleotide consisting of a base sequence having the deletion, substitution, insertion and/or addition of one to several bases in the base sequence set forth in SEQ ID NO: 1.

In the polynucleotide of (b), the term "one to several" bases may be, for example, one to ten, one to seven, one to five, one to three, one or two bases, or one base.

In the polynucleotide of (b), the term "base sequence having the deletion, substitution, insertion and/or addition of base(s)" is intended to encompass the meaning of a base sequence having the deletion, substitution, insertion and/or addition of base(s) with respect to the base sequence set forth in SEQ ID NO: 1 and the meaning of a base sequence having the deletion, substitution, insertion or addition of base(s) with respect to the base sequence set forth in SEQ ID NO: 1, or may be a base sequence having a difference of one to several bases due to at least one modification or mutation selected from the group consisting of deletion, substitution, insertion and addition, with respect to the base sequence set forth in SEQ ID NO: 1 prior to modification.

Generally, there may be a case where a polynucleotide consisting of a base sequence having a sequence identity to a polynucleotide also has the same function as the original polynucleotide. Further, as will be described in Examples to be given hereinafter, the present inventors have found that a nucleic acid having a polynucleotide in which the base sequence of the polynucleotide of (a) has been partially modified also has an ability to bind to an HGF receptor, similar to the polynucleotide of (a).

Thus, the aptamer according to one embodiment is an aptamer having the following polynucleotide of (c). (c) A polynucleotide consisting of a base sequence having a sequence identity of 80% or more to the base sequence set forth in SEQ ID NO: 1.

In the polynucleotide of (c), the sequence identity to the base sequence set forth in SEQ ID NO: 1 is 80% or more and less than 100%, and may be, for example, 85% or more, 90% or more, 95% or more, or 98% or more.

The sequence identity between base sequences can be calculated using a Basic Local Alignment Search Tool (BLAST) or blastn which is a known algorithm of sequence alignment.

The number of bases in the polynucleotides of (b) and (c) may be, for example, 28 to 35 bases, 30 to 33 bases, or 32 bases.

The aptamer of the present embodiment binds to an HGF receptor to exhibit an activity of inhibiting the binding of HGF to the HGF receptor.

Whether or not an aptamer will bind to an HGF receptor can be confirmed by a known binding assay method. For example, a labeled aptamer labeled by an appropriate label is prepared. After the HGF receptor is immobilized on a solid phase and a sample liquid containing the labeled aptamer is brought into contact with the solid phase, the sample liquid is removed from the solid phase, the solid phase is washed with a washing liquid, and then whether or not the label indicating the presence of the aptamer is detected on the solid phase is confirmed. In the case where the label is detected, it can be determined that the aptamer is bound to the HGF receptor and therefore the present aptamer has an ability to bind to the HGF receptor. The method to determine whether or not an aptamer has an ability to bind to an HGF receptor is not limited to the above method.

Whether or not an aptamer exhibits an activity of inhibiting the binding of HGF to the HGF receptor can be confirmed by a known binding assay method. For example, labeled HGF labeled by an appropriate label is prepared. A sample liquid A containing the labeled HGF but not containing an aptamer, and a sample liquid B containing the labeled HGF and an aptamer are prepared. After the HGF receptor is immobilized on a solid phase and the sample liquid A or sample liquid B is brought into contact with the solid phase, the sample liquid is removed from the solid phase, the solid phase is washed with a washing liquid, and values obtained by detecting the label on the solid phase are compared in the treatment of the sample liquid A and the treatment of the sample liquid B. A comparative experiment shall be carried out under the comparable same conditions. The value obtained by detecting the label indicates the binding of HGF to an HGF receptor. In the case where the value obtained by detecting the label is reduced in the solid phase brought into contact with the sample liquid B than in the solid phase brought into contact with the sample liquid A, it can be determined that the present aptamer exhibits an activity of inhibiting the binding of HGF to an HGF receptor. The method to determine whether or not an aptamer exhibits an activity of inhibiting the binding of HGF to an HGF receptor is not limited to the above method.

The aptamer according to one embodiment is an aptamer having a loop structure at least a part of which is formed of the polynucleotide of any of (a) to (c).

In the present specification, the term "loop structure" refers to a cyclic structure formed by bonding of one or more places of a chain-like compound to each other. For example, the loop structure may be a cyclic structure formed by base pairing of one or more sets of complementary bases in a single-stranded nucleic acid. The loop structure may be partially formed by the polynucleotide of any of (a) to (c) or may be formed of only the polynucleotide of any of (a) to (c). The means of bonding for forming a loop structure is not limited to a means by the formation of base pairs and may be, for example, a means by ligation of the 5' terminal and 3' terminal of a nucleic acid or a means by other arbitrary cross-linked structures. The term "loop structure" and the term "loop region" are used interchangeably.

FIG. 1 shows a schematic diagram of an aptamer according to one embodiment. An aptamer 2 consists of a polynucleotide and has a loop structure 20 which is at least partially formed of the polynucleotide 10 of any of (a) to (c).

Due to the fact that the aptamer has a loop structure, an ability to bind to an HGF receptor is improved.

The aptamer according to one embodiment may have a stem structure consisting of a double-stranded polynucleotide connected to the loop structure.

In the present specification, the term "stem structure" refers to a chain-like structure formed by bonding of two or more places of a chain-like compound to each other. For example, the stem structure may be a chain-like structure formed by base pairing of one or more sets of complementary bases in a single-stranded nucleic acid. The means of bonding for forming a stem structure is not limited to a means by the formation of base pairs and may be a means by other arbitrary cross-linked structures.

The connection embodiment of a stem structure to a loop structure is not particularly limited, but mention may be made of an embodiment formed of a polynucleotide in which a loop structure and a stem structure are consecutively connected. Such a form of nucleic acid is a structure commonly referred to as a "stem-loop structure" and is found in tRNA or the like. The stem structure is typified by a double-stranded polynucleotide formed by pairing of bases complementary to each other. The term "stem structure" and the term "stem region" are used interchangeably.

FIG. 1 shows a schematic diagram of an aptamer according to one embodiment. An aptamer 3 consists of a polynucleotide and has a loop structure 20 at least a part of which is formed of the polynucleotide 10 of any of (a) to (c) and a stem structure 30 consisting of a double-stranded polynucleotide which is connected by the loop structure 20. The loop structure contained in the aptamer may be only the loop structure 20.

Due to the fact that the aptamer has a stem structure consisting of a double-stranded polynucleotide, a loop structure can be easily formed and an ability to bind to an HGF receptor is improved.

The loop structure may consist of only a polynucleotide chain. In such a case, the loop structure may consist of a polynucleotide chain having 28 to 40 bases, may consist of a polynucleotide chain having 30 to 38 bases, may consist of a polynucleotide chain having 33 to 37 bases, or may consist of a polynucleotide chain having 36 bases.

The stem structure may consist of only a double-stranded polynucleotide. In such a case, one single-stranded polynucleotide forming the double-stranded polynucleotide may be a polynucleotide chain having 2 to 50 bases, a polynucleotide chain having 4 to 30 bases, or a polynucleotide chain having 5 to 15 bases.

In the aptamer according to one embodiment, the polynucleotide of (a) to (c) forms a guanine quadruplex structure. There may be a case where the guanine quadruplex structure is identified in a nucleic acid having an ability to bind to a target. As suggested by the name "guanine quadruplex", the guanine quadruplex structure is a specific three-dimensional structure which is formed by four sets of G sequences (see Y. Nonaka et al., Molecules, 25, pp 215 to 225 (2010)).

The guanine quadruplex can be classified into a "parallel-type" and an "antiparallel-type" depending on the topology thereof. Here, the guanine quadruplex structure formed of the polynucleotide of (a) to (c) may be a parallel-type or an antiparallel-type.

Whether or not a polynucleotide forms a guanine quadruplex structure can be confirmed by a known method. The presence of the parallel-type guanine quadruplex structure can be confirmed by detecting a negative peak at around 245 nm and a positive peak at around 265 nm, for example, by CD spectral measurement. Further, since the formation of a guanine quadruplex structure requires $K^+$ ions, for example, the identification of the guanine quadruplex structure can be carried out more reliably by comparing the results of CD spectral measurements for a polynucleotide in a solution containing $K^+$ ions and a polynucleotide in a solution not containing $K^+$ ions.

In terms of that a polynucleotide forms a guanine quadruplex structure, the polynucleotide of (a) to (c) may be a polynucleotide containing four or more sets of a sequence of two or more consecutive G's.

In the case where the aptamer according to one embodiment has a loop structure, the polynucleotide forming the loop structure may be a polynucleotide containing four or more sets of a sequence of two or more consecutive G's. As the polynucleotide containing four or more sets of a sequence of two or more consecutive G's, the polynucleotide of (a) is an exemplary example.

In the polynucleotide of (a) to (c), the base corresponding to a $3^{rd}$ base in the base sequence set forth in SEQ ID NO: 1 is preferably T or U.

In the polynucleotide of (a) to (c), the base corresponding to a $29^{th}$ base in the base sequence set forth in SEQ ID NO: 1 is preferably A, T or U.

In the polynucleotide of (b) and (c), the base corresponding to a $29^{th}$ base in the base sequence set forth in SEQ ID NO: 1 is preferably T or U.

As used herein, the term "base corresponding to" shall be determined in consideration of deletion, substitution, insertion and addition with respect to bases shown in SEQ ID NO: 1, and can be appropriately determined by comparing sequences by those skilled in the art.

As shown in Examples to be given hereinafter, the present inventors have found that a binding activity of an aptamer to an HGF receptor can be enhanced when the base of the above-mentioned position in the base sequence set forth in SEQ ID NO: 1 is set to the above-mentioned specific base.

It is particularly preferred that, in the polynucleotide of (a) to (c), the base corresponding to a $3^{rd}$ base in the base sequence set forth in SEQ ID NO: 1 is T or U, and in the polynucleotide of (b) and (c), the base corresponding to a $29^{th}$ base in the base sequence set forth in SEQ ID NO: 1 is T or U.

Here, in the case where the nucleotide having a $3^{rd}$ base is a deoxyribonucleotide, T is selected as the base corresponding to a $3^{rd}$ base. In the case where the nucleotide having a $29^{th}$ base is a deoxyribonucleotide, T is selected as the base corresponding to a $29^{th}$ base.

The polynucleotide of (a) to (c) may be DNA. The nucleotide constituting the polynucleotide of (a) to (c) may be a nucleotide containing DNA at least in a part thereof, and the nucleotide constituting the polynucleotide of (a) to (c) may be of only DNA.

The polynucleotide forming a loop structure may be DNA. The nucleotide constituting a loop structure may be a nucleotide containing DNA at least in a part thereof, and the nucleotide constituting a loop structure may be of only DNA.

The polynucleotide forming an aptamer of one embodiment may be DNA. The nucleotide constituting an aptamer of one embodiment may be a nucleotide containing DNA at least in a part thereof, and the nucleotide constituting an aptamer of one embodiment may be of only DNA.

The number of bases in a polynucleotide contained in an aptamer according to one embodiment may be 500 bases or less, 250 bases or less, 150 bases or less, 80 bases or less, 70 bases or less, 60 bases or less, or 55 bases or less.

The number of bases in a polynucleotide contained in an aptamer according to one embodiment may be 28 bases or more, 35 bases or more, 40 bases or more, or 45 bases or more.

The number of bases in a polynucleotide contained in an aptamer according to one embodiment may be, for example, 28 to 500 bases, 35 to 250 bases, 40 to 150 bases, 40 to 150 bases, 40 to 80 bases, 40 to 70 bases, 40 to 60 bases, or 45 to 55 bases.

With regard to the aptamer of the foregoing embodiment, an aptamer in which a certain material is further added to the polynucleotide of any of (a) to (c) is also encompassed by the aptamer of the present embodiment, as long as it has the polynucleotide of any of (a) to (c) and binds to an HGF receptor to exhibit an activity of inhibiting the binding of HGF to the HGF receptor. For example, such an aptamer may be an aptamer with various modifications to enhance in vivo stability, or an aptamer with addition of labels such as dyes.

Incidentally, the aptamer of the foregoing embodiments is intended to be defined on the basis of the base sequence set forth in SEQ ID NO: 1, but it may be defined on the basis of base sequence 2, base sequence 3 or base sequence 4 in place of the base sequence 1.

Aptamers of embodiments can be produced by known techniques. Techniques of nucleic acid synthesis and methods of nucleic acid modification are widely used in the field of life science.

«Multi-Structure Aptamer»

The multi-structure aptamer according to the present embodiment is an aptamer having a multi-structure in which two or more members of one unit of an aptamer are connected, taking the aptamer of the embodiment described in the foregoing section «Aptamer» as one unit. In the present specification, such an aptamer having a multi-structure may be referred to as a "multi-structure aptamer". The multi-structure aptamer may be, for example, a dimer in which two members of one unit of an aptamer are connected.

The connected aptamers may be the same or different from each other. Hereinafter, the description of the contents overlapping with the contents described in the foregoing section «Aptamer» is omitted.

The multi-structure aptamer according to one embodiment has a multi-structure in which two or more polynucleotides of any of the following (a) to (c) are connected, and binds to an HGF receptor to exhibit an activity of activating the HGF receptor.

(a) A polynucleotide consisting of a base sequence set forth in SEQ ID NO: 1, (b) A polynucleotide consisting of a base sequence having the deletion, substitution, insertion and/or addition of one to several bases in the base sequence set forth in SEQ ID NO: 1, and (c) A polynucleotide consisting of a base sequence having a sequence identity of 80% or more to the base sequence set forth in SEQ ID NO: 1.

The polynucleotide of any of (a) to (c) is the same as that described in the foregoing section «Aptamer» and therefore a description thereof is omitted.

In the multi-structure aptamer according to one embodiment, it may have a stem structure consisting of a double-stranded polynucleotide connected to the loop structure.

In the multi-structure aptamer according to one embodiment, it may be an aptamer in which the loop structure consists of a polynucleotide chain having 28 to 40 bases.

In the multi-structure aptamer according to one embodiment, the polynucleotide of (a) to (c) may have a guanine quadruplex structure.

In the multi-structure aptamer according to one embodiment, the polynucleotide of (a) to (c) may also contain four or more sets of a sequence of two or more consecutive G's.

In the multi-structure aptamer according to one embodiment, the polynucleotide of (a) to (c) may be DNA.

Figure 2:
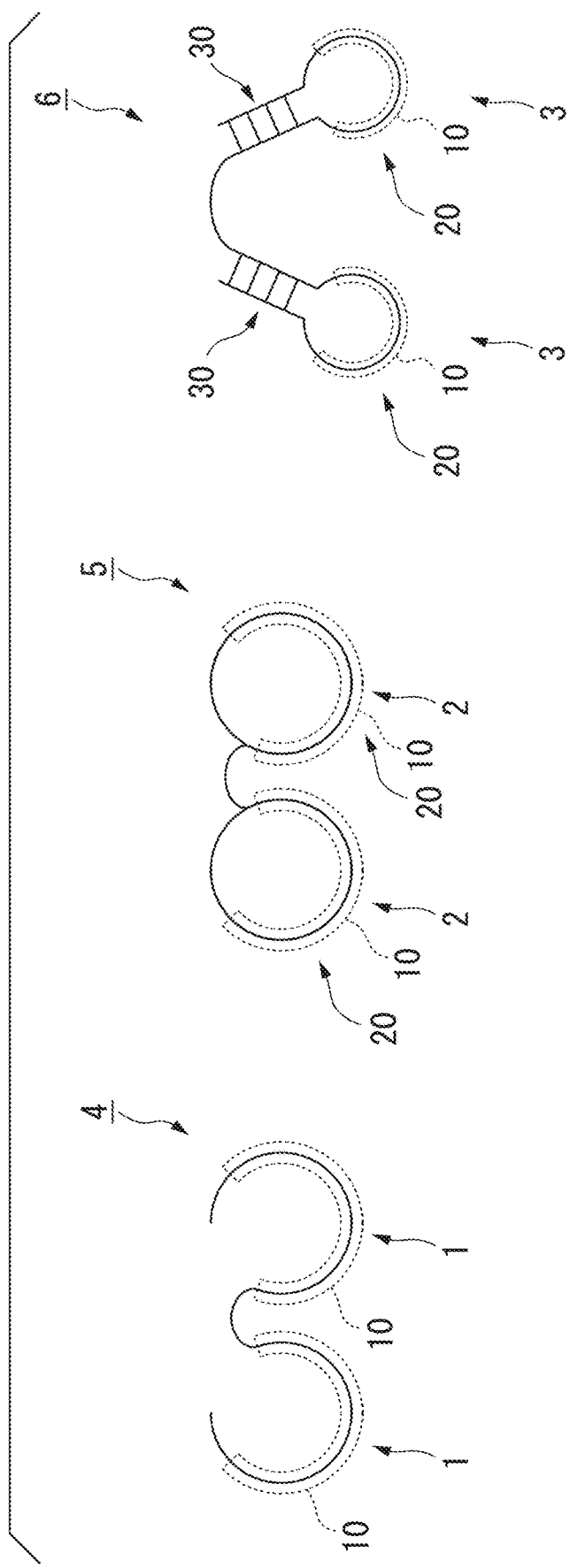
FIG. 2 is a schematic diagram of a multi-structure aptamer in one embodiment.

FIG. 2 shows a schematic diagram of a multi-structure aptamer according to one embodiment. A multi-structure aptamer 4 consists of a polynucleotide, and has a multi-structure in which two or more polynucleotides 10 of any of (a) to (c) are connected. The multi-structure aptamer 4 is an aptamer in which two members of one unit of an aptamer 1 are connected.

The polynucleotides 10 may be polynucleotides having the same base sequence. For example, both of two polynucleotides 10 may be the polynucleotides of (a).

Alternatively, the polynucleotides 10 may be polynucleotides each of which has a different base sequence. For example, one of two polynucleotides 10 may be the polynucleotide of (a) and the other one of two polynucleotides 10 may be the polynucleotide of (b).

The multi-structure aptamer of the present embodiment binds to an HGF receptor to exhibit an activity of activating the HGF receptor.

Whether or not an aptamer binds to an HGF receptor was described in the foregoing section «Aptamer» and therefore a description thereof is omitted.

The activation state of the HGF receptor can be confirmed by a known detection method. The activation of the HGF receptor can be detected, for example, by detecting phosphorylation of the HGF receptor. The phosphorylation of the HGF receptor is detectable using a known antibody capable of specifically detecting the phosphorylation of the HGF receptor.

Whether or not an aptamer has an activity of activating an HGF receptor can be confirmed by a known detection method. For example, a sample liquid C containing an HGF receptor-expressing cell and not containing an aptamer, and a sample liquid D containing an HGF receptor-expressing cell and an aptamer are prepared. After culturing cells in each sample liquid, values indicating phosphorylation of an HGF receptor are compared in the treatment of the sample liquid C and the treatment of the sample liquid D. A comparative experiment shall be carried out under the comparable same conditions. In the case where the value indicating the phosphorylation of an HGF receptor in the sample liquid D is higher than the value indicating the phosphorylation of an HGF receptor in the sample liquid C, it can be determined that the present aptamer has an activity of activating an HGF receptor. Incidentally, the method of determining that an aptamer has an activity of activating an HGF receptor is not limited to the above-mentioned method.

The multi-structure aptamer according to one embodiment may have a multi-loop structure in which two or more loop structures at least a part of which is formed of the polynucleotide of any of (a) to (c) are connected.

The description of the loop structure is omitted because description thereof has been made in the foregoing section «Aptamer».

FIG. 2 shows a schematic diagram of a multi-structure aptamer according to one embodiment. A multi-structure aptamer 5 consists of a polynucleotide, and has a multi-loop structure in which two or more loop structures 20 at least a part of which is formed of the polynucleotide 10 of any of (a) to (c) are connected. Thus, the multi-structure aptamer 5 is an aptamer in which two members of one unit of an aptamer 2 having a loop structure 20 are connected.

The multi-structure aptamer according to one embodiment has a stem structure consisting of a double-stranded polynucleotide connected to the loop structure.

FIG. 2 shows a schematic diagram of a multi-structure aptamer according to one embodiment. A multi-structure aptamer 6 consists of a polynucleotide, and has a multi-loop structure in which two or more structures having a loop structure 20 at least a part of which is formed of the polynucleotide 10 of any of (a) to (c) and a stem structure 30 consisting of a double-stranded polynucleotide connected by the loop structure 20 are connected.

Thus, the multi-structure aptamer 6 is an aptamer in which two members of one unit of an aptamer 3 having a loop structure 20 and a stem structure 30 are connected.

In this way, in the case of having a plurality of stem structures in the molecule, the base sequences forming the respective stem structures may be of sequences different from each other. In the case where two or more base sequences forming identical stem structures are present in the molecule, there is a possibility that the counterpart nucleotide chain forming a complementary strand is interchanged. In this regard, by setting the base sequences forming the respective stem structures to be sequences different from each other, the counterpart nucleotide chain forming a complementary strand is prevented from being interchanged. It should be noted that such a modification is not essential, and the aptamers are also functional even in a multi-structure aptamer in which completely same stem structures or completely same aptamer sequences are allowed to be consecutive.

Figure 3:
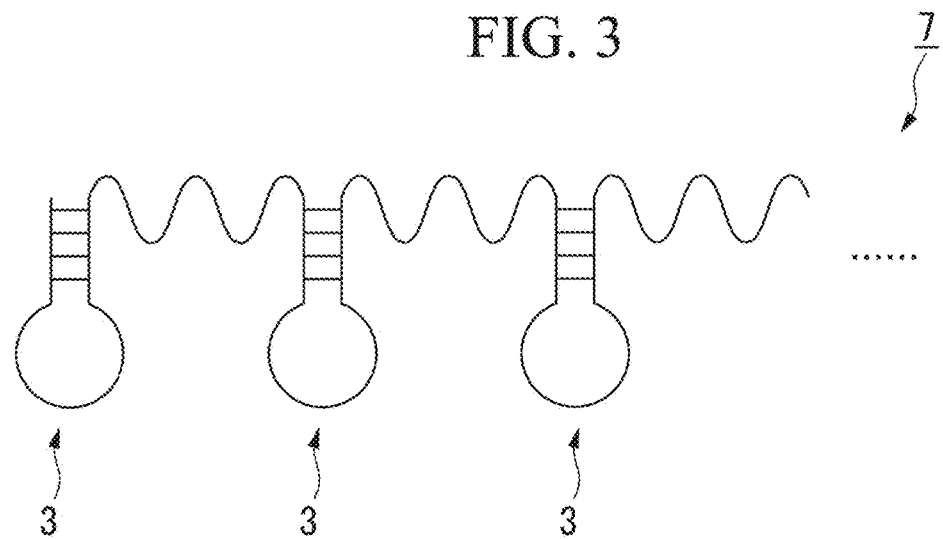
FIG. 3 is a schematic diagram of a multi-structure aptamer in one embodiment.
Figure 4:
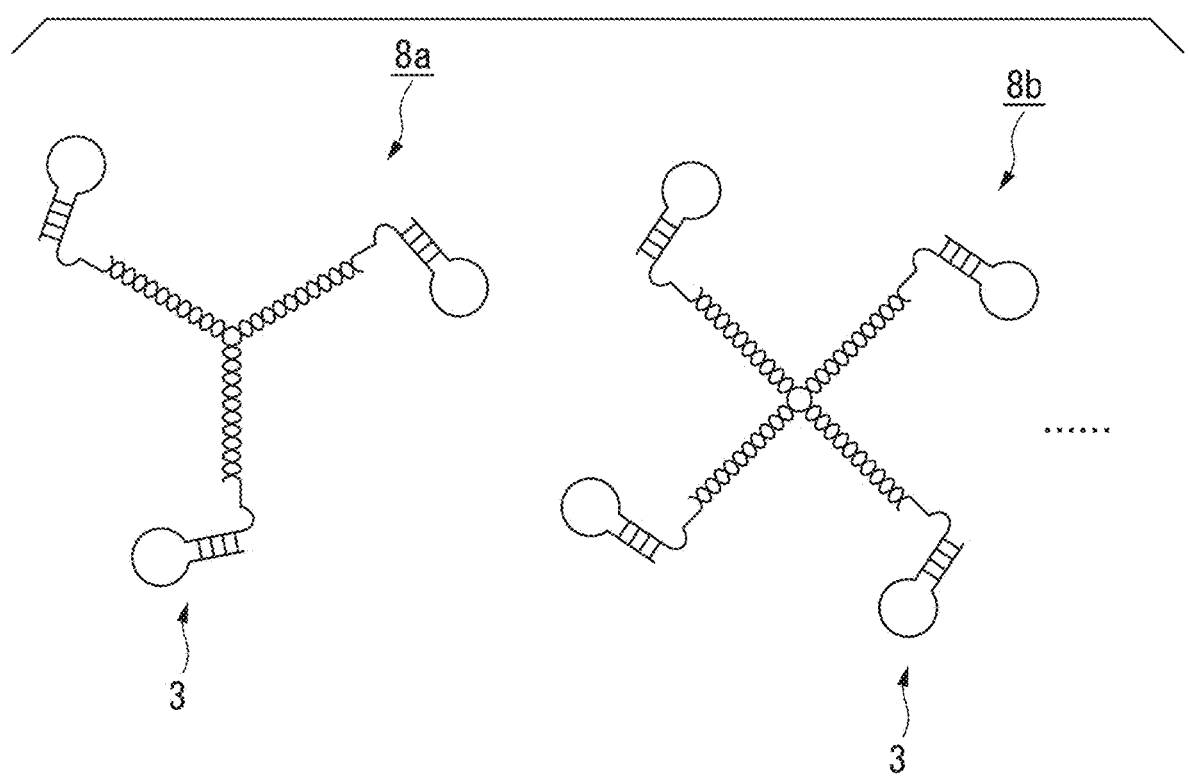
FIG. 4 is a schematic diagram of a multi-structure aptamer in one embodiment.

FIGS. 3 and 4 schematically show an example of an embodiment of a multi-structure aptamer. A multi-structure aptamer 7 shown in FIG. 3 is an aptamer in which three or more members of one unit of an aptamer 3 are connected in parallel. Multi-structure aptamers 8a and 8b shown in FIG. 4 are aptamers in which three or more members of one unit of an aptamer 3 are connected in a radial fashion.

The polynucleotide forming a multi-structure aptamer of one embodiment may be DNA. The nucleotide constituting a multi-structure aptamer of one embodiment may be a nucleotide containing DNA at least in a part thereof, and the nucleotide constituting a multi-structure aptamer of one embodiment may be of only DNA.

The multi-structure aptamer according to one embodiment may be configured in such a manner that two or more polynucleotides of (a) to (c) are connected by a linker, and the length of the linker is 80 bases or less in terms of polynucleotide.

Figure 5:
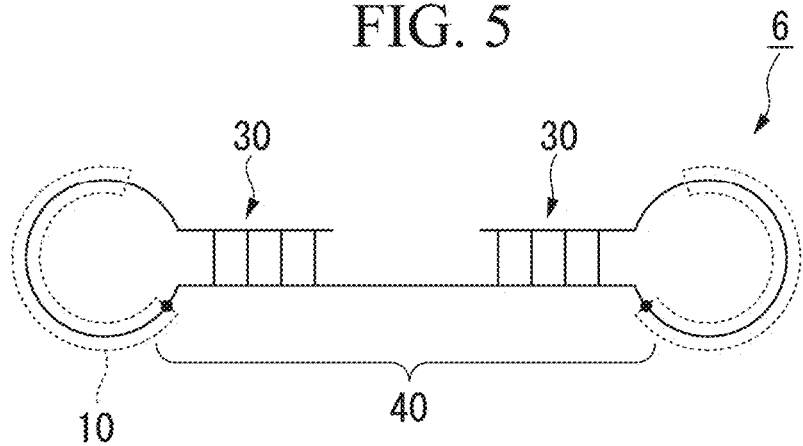
FIG. 5 is a schematic diagram of a multi-structure aptamer in one embodiment.

FIG. 5 shows a linker of a multi-structure aptamer, by way of example of a multi-structure aptamer 6. A linker 40 is a region between the terminals of the polynucleotide 10 of (a) to (c). In the case where the aptamer has a stem structure 30, the stem structure is also intended to be included in the part of the linker. The length of the linker may be 80 bases or less in terms of polynucleotide. The linker may be formed of a material other than a polynucleotide. For example, the material other than a polynucleotide may be, for example, polyethylene glycol (PEG). In the case where the linker is formed of a material other than a polynucleotide, the length of the linker shall be calculated based on the length of the polynucleotide. The length of the reference polynucleotide shall be calculated based on the distance between base pairs of 3.4 angstrom in DNA having a double helix structure. 1 angstrom is 0.1 nm.

The length of the linker may be a length of 0 to 80 bases, a length of 5 to 70 bases, a length of 10 to 60 bases, a length of 15 to 50 bases, a length of 15 to 30 bases, or a length of 16 to 20 bases in terms of polynucleotide.

With regard to the multi-structure aptamer according to one embodiment, the number of bases in the polynucleotide contained in the aptamer may be 1000 bases or less, 700 bases or less, 500 bases or less, 250 bases or less, 150 bases or less, 100 bases or less, 80 bases or less, or 60 bases or less.

The number of bases in the polynucleotide contained in the multi-structure aptamer according to one embodiment may be 56 bases or more, 60 bases or more, 80 bases or more, 100 bases or more, or 200 bases or more.

The number of bases in the polynucleotide contained in the multi-structure aptamer according to one embodiment may be, for example, 56 to 1000 bases, 60 to 700 bases, 80 to 500 bases, 90 to 250 bases, 90 to 150 bases, or 90 to 100 bases.

With regard to the multi-structure aptamer of the foregoing embodiment, an aptamer where a certain material is further added to a multi-structure in which two or more polynucleotides of any of (a) to (c) have been connected is also encompassed by the multi-structure aptamer of the present embodiment, as long as it has a multi-structure in which two or more polynucleotides of any of (a) to (c) are connected and binds to an HGF receptor to exhibit an activity of activating the HGF receptor. For example, such an aptamer may be an aptamer with various modifications to enhance in vivo stability, or an aptamer with addition of labels such as dyes.

Multi-structure aptamers of embodiments can be produced by known techniques. Techniques of nucleic acid synthesis and methods of nucleic acid modification are widely used in the field of life science.

«Aptamer-Immobilized Carrier»

As one embodiment of the present invention, an aptamer-immobilized carrier in which the aptamer or multi-structure aptamer of the foregoing embodiment is immobilized on the surface of a solid phase carrier is an exemplary example.

As the solid phase carrier, it is possible to employ carriers of various shapes such as sheet-like, plate-like, cylindrical, and spherical carriers. As the material for a carrier, plastic, metal, glass or the like is an exemplary example. Any material may be employed as long as it is a material capable of immobilizing an aptamer.

Figure 6:
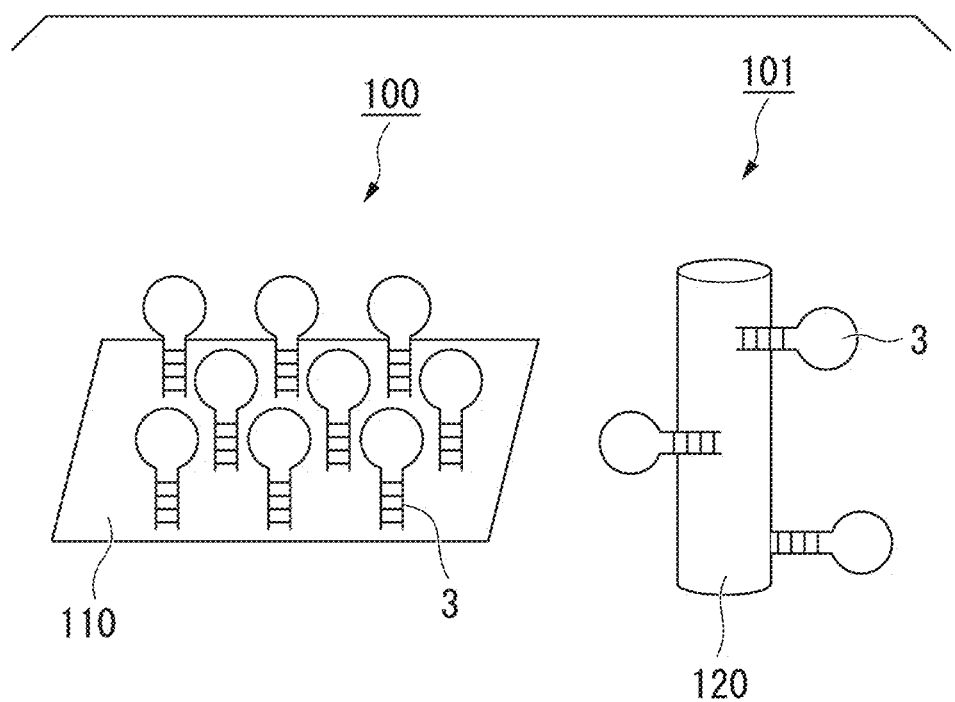
FIG. 6 is a schematic diagram of an aptamer-immobilized carrier in one embodiment.

FIG. 6 schematically shows an example of an embodiment of the aptamer-immobilized carrier. An aptamer-immobilized carrier 100 is a carrier in which an aptamer 3 is immobilized on the surface of a sheet-like solid phase carrier 110. An aptamer-immobilized carrier 101 is a carrier in which an aptamer 3 is immobilized on the surface of a cylindrical solid phase carrier 120.

The aptamer-immobilized carrier in which two or more polynucleotides of any of (a) to (c) are connected on a solid phase and which binds to an HGF receptor to exhibit an activity of activating the HGF receptor may be treated as the foregoing multi-structure aptamer.

«Formulation and Composition»

As one embodiment of the present invention, provided is an agent containing the aptamer or multi-structure aptamer of the foregoing embodiment as an active ingredient for treating or preventing an HGF receptor signaling-related disease.

By administering the aptamer according to the foregoing embodiment to a living subject, it is possible to control HGF receptor signaling. As a result, it is possible to treat or prevent an HGF receptor signaling-related disease. The HGF receptor signaling-related disease may be, for example, cancer and the like.

In one embodiment, the present invention provides a method for treating or preventing an HGF receptor signaling-related disease, including a step of administering an effective amount of the aptamer or multi-structure aptamer of the foregoing embodiment to a human or animal subject in need of treatment.

In one embodiment, the present invention provides the aptamer or multi-structure aptamer of the foregoing embodiment for the treatment or prevention of an HGF receptor signaling-related disease.

In one embodiment, the present invention provides use of the aptamer or multi-structure aptamer of the foregoing embodiment for the manufacture of an agent for treating or preventing an HGF receptor signaling-related disease.

As one embodiment of the present invention, provided is an agent for inhibiting metastasis of a cancer cell, containing the multi-structure aptamer of the foregoing embodiment as an active ingredient.

As shown in Examples to be given hereinafter, the present inventors have found that it is possible to inhibit migration of cancer cells by way of an SL1 dimer (multi-structure aptamer). Because, it is possible to inhibit migration of cancer cells by way of a multi-structure aptamer, the multi-structure aptamer according to one embodiment of the present invention is understood to have an antimetastatic activity against cancer cells.

In one embodiment, the present invention provides a method for inhibiting metastasis of a cancer cell, including a step of administering an effective amount of the multi-structure aptamer of the foregoing embodiment to a human or animal subject in need of treatment.

In one embodiment, the present invention provides the multi-structure aptamer of the foregoing embodiment for inhibiting metastasis of a cancer cell.

In one embodiment, the present invention provides use of the multi-structure aptamer of the foregoing embodiment for the manufacture of an agent for inhibiting metastasis of a cancer cell.

The agent for treating or preventing an HGF receptor signaling-related disease, or the agent for inhibiting metastasis of a cancer cell may be administered by itself or may be administered as a pharmaceutical composition in admixture with a suitable pharmacologically acceptable additive, in the form of a formulation such as a tablet, a capsule, or a granule via an oral route or in the form of a formulation such as an injection or a suppository via a parenteral route.

These formulations can be prepared by a known method, using additives such as an excipient, a binding agent, a disintegrating agent, a lubricant, an emulsifier, a stabilizer, a diluent, and a solvent for injection.

Examples of the excipient include an organic excipient and an inorganic excipient. Examples of the organic excipient include a sugar derivative such as lactose or sucrose; a starch derivative such as corn starch or potato starch; a cellulose derivative such as crystalline cellulose; and gum arabic. Examples of the inorganic excipient include a sulfate such as calcium sulfate.

Examples of the binding agent include the foregoing excipient, gelatin, polyvinylpyrrolidone, and polyethylene glycol.

Examples of the disintegrating agent include the foregoing excipient; a derivative of starch or cellulose such as croscarmellose sodium or sodium carboxymethyl starch; and cross-linked polyvinylpyrrolidone.

Examples of the lubricant include talc; stearic acid; colloidal silica; waxes such as beads wax and spermaceti; a sulfate such as sodium sulfate; a lauryl sulfate such as sodium lauryl sulfate; and a starch derivative in the foregoing excipient.

Examples of the emulsifier include a colloidal clay such as bentonite or Veegum; an anionic surfactant such as sodium lauryl sulfate; a cationic surfactant such as benzalkonium chloride; and a nonionic surfactant such as polyoxyethylene alkyl ether.

Examples of the stabilizer include p-hydroxybenzoic acid esters such as methylparaben and propylparaben; alcohols such as chlorobutanol; and phenols such as phenol and cresol.

Examples of the diluent include water, ethanol, and propylene glycol.

The solvent for injection include water, ethanol, and glycerin.

The dose of the aptamer or multi-structure aptamer of the foregoing embodiment may vary depending on symptoms. In the case of oral administration, the dose of the aptamer or multi-structure aptamer may be usually, for example, about 0.1 to 100 mg/day, for an adult (body weight of 60 kg).

In the case of parenteral administration, the single dose of the aptamer or multi-structure aptamer may vary depending on the subject to be administered, target organ, symptoms, and administration method. For example, when it is desired to administer the aptamer or multi-structure aptamer in the form of an injection to an adult (body weight of 60 kg), the aptamer or multi-structure aptamer may be administered by intravenous injection or local injection of, for example, about 0.01 to 30 mg/day.

The aptamers of the foregoing embodiments contained in the agent for treating or preventing an HGF receptor signaling-related disease or the agent for inhibiting metastasis of a cancer cell may be in the form of a vector capable of expressing these aptamers.

As one embodiment of the present invention, provided is a cell culture composition containing the aptamer or multi-structure aptamer of the foregoing embodiment.

By culturing cells in a medium (cell culture composition) containing the aptamer according to the foregoing embodiment, it is possible to control a variety of cell states involved in HGF receptor signaling, such as differentiation, growth, migration and the like of cells.

The cell culture composition may be a composition in which an aptamer itself is added to a medium of cells, or may be provided to the cells as a composition in which an aptamer and an appropriate diluent are mixed. Examples of the diluent include water, buffers, and various media.

The concentration of the aptamer contained in the cell culture composition may be, for example, 0.01 nM to 10 µM, 0.1 nM to 5 µM, 1 nM to 5 µM, 50 nM to 3 µM, or 100 nM to 2 µM, and is preferably 0.1 nM or more. M represents mol/L.

«Method»

(Detection Method)

As one embodiment of the present invention, provided is a method for detecting an HGF receptor, including binding the aptamer of the foregoing embodiment to the HGF receptor to thereby detect the HGF receptor.

Here, the aptamer may be labeled with a labeling substance, and it may detect the HGF receptor by detecting the labeling substance. Examples of the labeling substance include a dye, a fluorescent dye, a radioisotope, an antibody, an antigen, and an enzyme. Examples of the fluorescent dye include FITC.

(Cell Culture Method)

As one embodiment of the present invention, provided is a cell culture method including culturing an HGF receptor-expressing cell in a medium containing the aptamer or multi-structure aptamer of the foregoing embodiment.

The cell culture may employ the foregoing cell culture composition, and an HGF receptor-expressing cell may be cultured in the foregoing cell culture composition.

(Method for Inhibiting Binding)

As one embodiment of the present invention, provided is a method for inhibiting the binding of HGF to an HGF receptor, including bringing the aptamer of the foregoing embodiment into contact with an HGF receptor-expressing cell.

With respect to whether or not an aptamer inhibits the binding of HGF to an HGF receptor, it can be determined that the aptamer inhibits the binding of HGF to an HGF receptor, for example, in the case where cells brought into contact with the aptamer and cells not brought into contact with the aptamer are compared and then the degree of binding of HGF to the HGF receptor is reduced in the cells brought into contact with the aptamer.

(Method for Inhibiting Differentiation)

As one embodiment of the present invention, provided is a method for inhibiting differentiation of a cell, including bringing the aptamer of the foregoing embodiment into contact with an HGF receptor-expressing cell.

With respect to whether or not an aptamer inhibits differentiation of cells, it can be determined that the aptamer inhibits differentiation of cells, for example, in the case where cells brought into contact with the aptamer and cells not brought into contact with the aptamer are compared and then a change in the differentiation state of cells is smaller in the cells brought into contact with the aptamer.

(Method for Inhibiting Growth)

As one embodiment of the present invention, provided is a method for inhibiting growth of a cell, including bringing the aptamer of the foregoing embodiment into contact with an HGF receptor-expressing cell.

With respect to whether or not an aptamer inhibits growth of cells, it can be determined that the aptamer inhibits growth of cells, for example, in the case where cells brought into contact with the aptamer and cells not brought into contact with the aptamer are compared and then the degree of cell growth is smaller in the cells brought into contact with the aptamer.

(Method for Inhibiting Migration)

As one embodiment of the present invention, provided is a method for inhibiting migration of a cell, including bringing the aptamer of the foregoing embodiment into contact with an HGF receptor-expressing cell.

With respect to whether or not an aptamer inhibits migration of cells, it can be determined that the aptamer inhibits migration of cells, for example, in the case where cells brought into contact with the aptamer and cells not brought into contact with the aptamer are compared and then the degree of cell migration is smaller in the cells brought into contact with the aptamer.

(Method for Activating HGF Receptor)

As one embodiment of the present invention, provided is a method for activating an HGF receptor, including bringing the multi-structure aptamer of the foregoing embodiment into contact with an HGF receptor-expressing cell.

With respect to whether or not a multi-structure aptamer activates an HGF receptor, it can be determined that the aptamer activates the HGF receptor, for example, in the case where cells brought into contact with the multi-structure aptamer and cells not brought into contact with the multi-structure aptamer are compared and then the degree of phosphorylation of the HGF receptor is larger in the cells brought into contact with the multi-structure aptamer.

(Method for Inducing Differentiation)

As one embodiment of the present invention, provided is a method for inducing differentiation of a cell, including bringing the multi-structure aptamer of the foregoing embodiment into contact with an HGF receptor-expressing cell.

With respect to whether or not a multi-structure aptamer induces differentiation of cells, it can be determined that the aptamer induces differentiation of cells, for example, in the case where cells brought into contact with the multi-structure aptamer and cells not brought into contact with the multi-structure aptamer are compared and then a change in the differentiation state of cells is larger in the cells brought into contact with the multi-structure aptamer.

(Method for Promoting Growth)

As one embodiment of the present invention, provided is a method for promoting growth of a cell, including bringing the multi-structure aptamer of the foregoing embodiment into contact with an HGF receptor-expressing cell.

With respect to whether or not a multi-structure aptamer promotes growth of cells, it can be determined that the aptamer promotes growth of cells, for example, in the case where cells brought into contact with the multi-structure aptamer and cells not brought into contact with the multi-structure aptamer are compared and then the degree of cell growth is larger in the cells brought into contact with the multi-structure aptamer.

(Method for Promoting Migration)

As one embodiment of the present invention, provided is a method for promoting migration of a cell, including bringing the multi-structure aptamer of the foregoing embodiment into contact with an HGF receptor-expressing cell.

With respect to whether or not a multi-structure aptamer promotes migration of cells, it can be determined that the aptamer promotes migration of cells, for example, in the case where cells brought into contact with the multi-structure aptamer and cells not brought into contact with the multi-structure aptamer are compared and then the degree of cell migration is larger in the cells brought into contact with the multi-structure aptamer.

Bringing of an aptamer into contact with an HGF receptor-expressing cell results in binding of the aptamer to an HGF receptor.

Here, the method of bringing an aptamer into contact with an HGF receptor-expressing cell is not particularly limited and it is possible to use various methods. Examples of the method of bringing an aptamer into contact with an HGF receptor-expressing cell include a method of bringing an aptamer into contact with cells by culturing the cells in a medium containing the aptamer, a method of bringing an aptamer into contact with cells by including the aptamer and the cells in the same solution, and a method of dropping an aptamer-containing composition to cells.

The method of bringing an aptamer into contact with an HGF receptor-expressing cell may be carried out in vivo or in vitro, and is preferably carried out in vitro.

Hereinafter, the present invention will be described by way of the following Examples, but the present invention is not limited thereto.

EXAMPLES (SL1)

A polynucleotide consisting of a base sequence set forth in SEQ ID NO: 1, a polynucleotide consisting of a base sequence set forth in SEQ ID NO: 5, and a polynucleotide consisting of a base sequence set forth in SEQ ID NO: 6 were synthesized.

Figure 7:
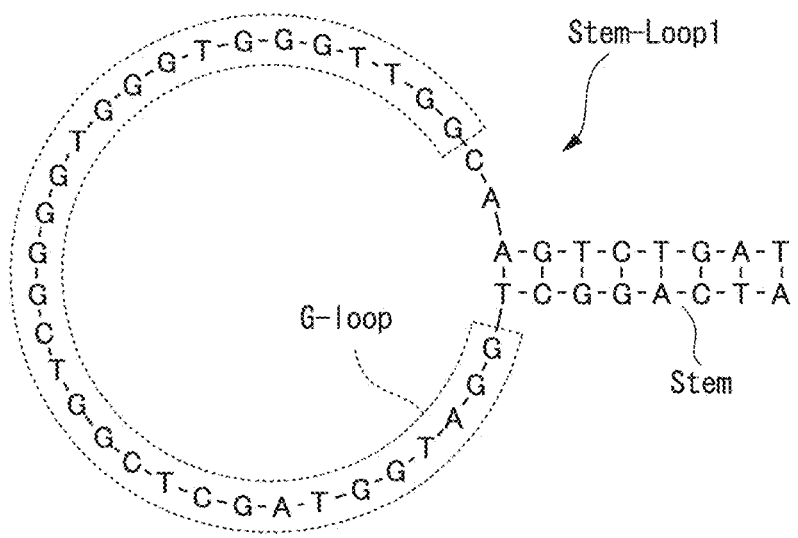
FIG. 7 is a diagram showing a structure of SL1 (aptamer) constructed in Examples.

The polynucleotide according to SEQ ID NO: 1 forms a G-loop shown in FIG. 7.

The polynucleotide according to SEQ ID NO: 5 forms a Stem-Loop1 shown in FIG. 7.

The polynucleotide according to SEQ ID NO: 6 is a Stem-Loop1 reverse sequence which is a reverse sequence of Stem-Loop1 and was prepared as a Negative Control.

Figure 8:
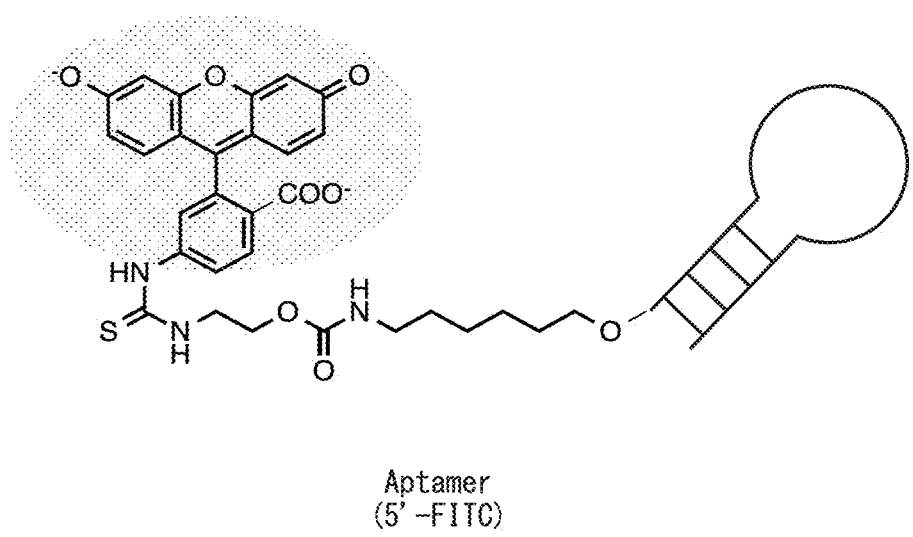
FIG. 8 is a schematic diagram showing a structure of FITC-labeled SL1 constructed in Examples.

Each polynucleotide of the Stem-Loop1, G-loop, and Stem-Loop1 reverse sequence was labeled with fluorescein• isothiocyanate (FITC) (FIG. 8). The FITC-labeled polynucleotide was obtained by custom synthesis from FAS-MAC Co., Ltd.

SNU-5 cells were immersed in a liquid containing the FITC-labeled Stem-Loop1 at a concentration of 100 nM and allowed to react for 15 minutes at 21° C. The SNU-5 cell is a strain expressing c-Met (HGF receptor). In addition, the same procedure was also carried out for the system using the FITC-labeled G-loop or the FITC-labeled Stem-Loop1 reverse sequence in place of the FITC-labeled Stem-Loop1. As another control, SNU-5 cells which had been treated with none of the above-described FITC-labeled polynucleotides were prepared. This control is simply denoted by Cell in FIG. 3 to be described hereinafter. Then, the fluorescence intensity of FITC in cells of each system was measured using a flow cytometer.

Figure 9:
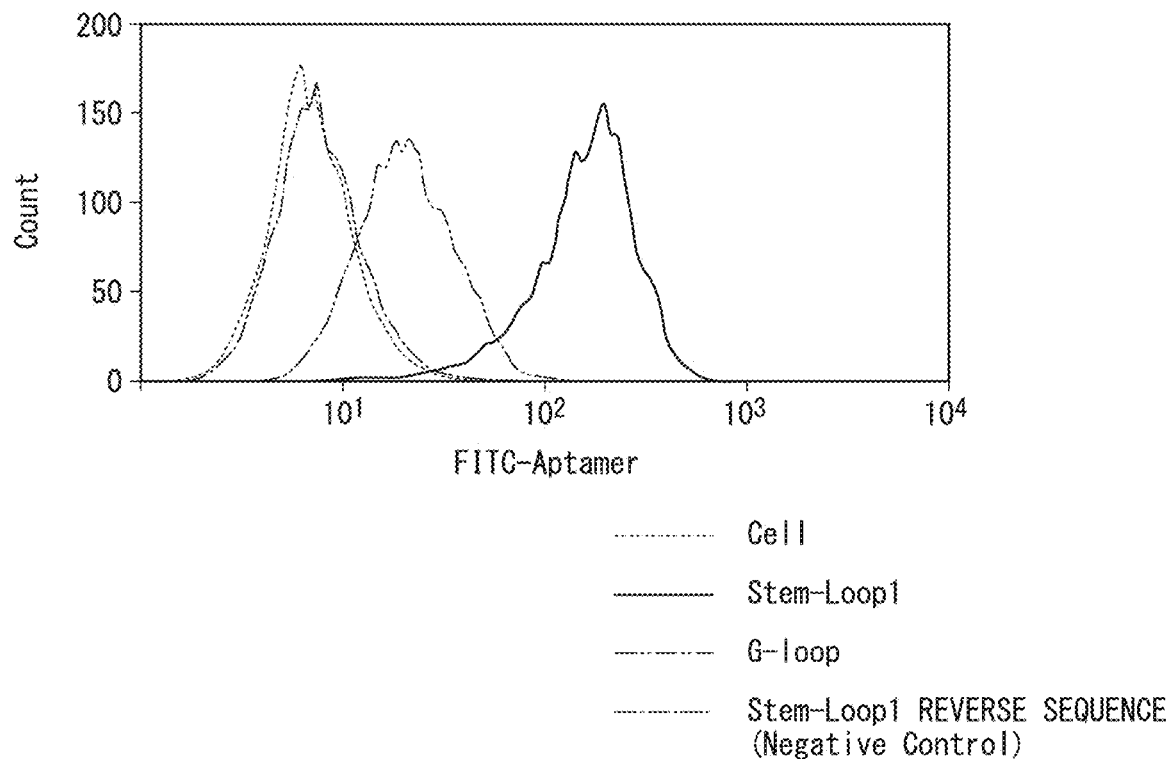
FIG. 9 is a diagram of the results showing an ability of SL1 to bind to an HGF receptor, obtained in Examples.

The results are shown in FIG. 9. FITC-labeled Stem-Loop1 reverse sequence-treated SNU-5 cells (Stem-Loop1 reverse sequence) exhibited a distribution of the same fluorescence intensity as that of Control SNU-5 cells (Cell). Therefore, it was suggested that the Stem-Loop1 reverse sequence does not bind to or hardly binds to an HGF receptor. FITC-labeled G-loop-treated SNU-5 cells (G-loop) exhibited a fluorescence intensity distribution of a value higher than that of Control SNU-5 cells (Cell). Therefore, it was suggested that the G-loop has an ability to bind to an HGF receptor. FITC-labeled Stem-Loop1-treated. SNU-5 cells (Stem-Loop1) exhibited a fluorescence intensity distribution of a value higher than that of FITC-labeled G-loop-treated SNU-5 cells (G-loop). Therefore, it was suggested that the Stem-Loop1 has a higher ability to bind to an HGF receptor than that of the G-loop.

Next, the Stem-Loop1 (herein sometimes referred to simply as "SL1") was analyzed in more detail. SNU-5 cells were immersed in a liquid containing FITC-labeled SL1 at each of the following concentrations of (0 nM (Cell), 2.5 nM, 10 nM, 25 nM, 100 nM, 250 nM, or 1000 nM) and allowed to react at 21° C. for 15 minutes. Then, the fluorescence intensity of the cells after the reaction was measured.

Figure 10:
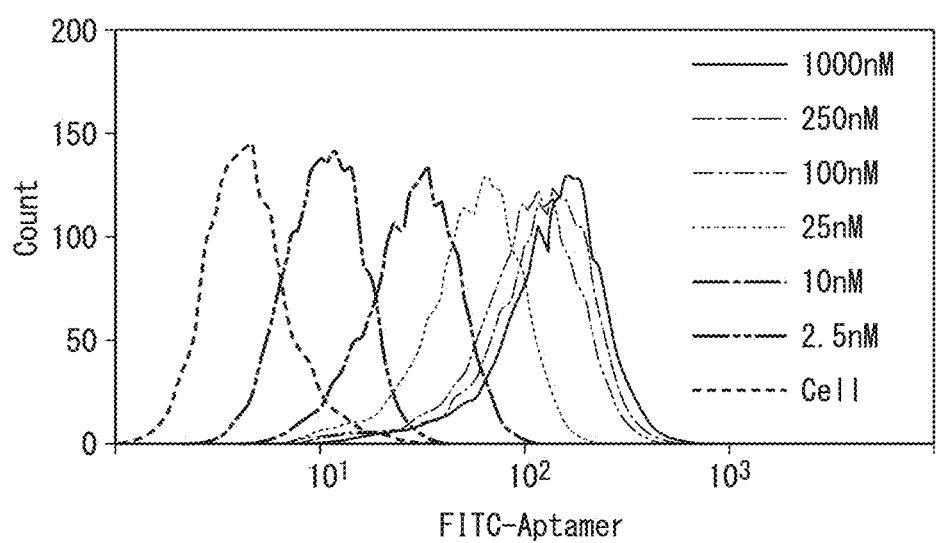
FIG. 10 is a diagram of the results showing an ability of SL1 to bind to an HGF receptor, obtained in Examples.

The results are shown in FIG. 10. As the concentration of SL1 in the liquid is increased, the fluorescence intensity distribution of SNU-5 cells becomes a higher value, with almost no change at a value of 1000 nM.

Whether or not SL1 has a guanine quadruplex structure was verified. It has been known that at least four sets of two or more consecutive G's are required as the conditions for forming a guanine quadruplex structure. The presence of a parallel-type guanine quadruplex structure can be demonstrated by detection of a negative peak at around 245 nm and a positive peak at around 264 nm through CD spectral measurement. In addition, the formation of a guanine quadruplex structure requires $K^+$ ions.

A 20 mM Tris-HCl buffer containing 5 μM of SL1 (SL1) and a 20 mM Tris-HCl buffer containing 5 μM of SL1 and 5 mM of KCl (SL1+5 mM KCl) were subjected to a CD spectral analysis.

Figure 11:
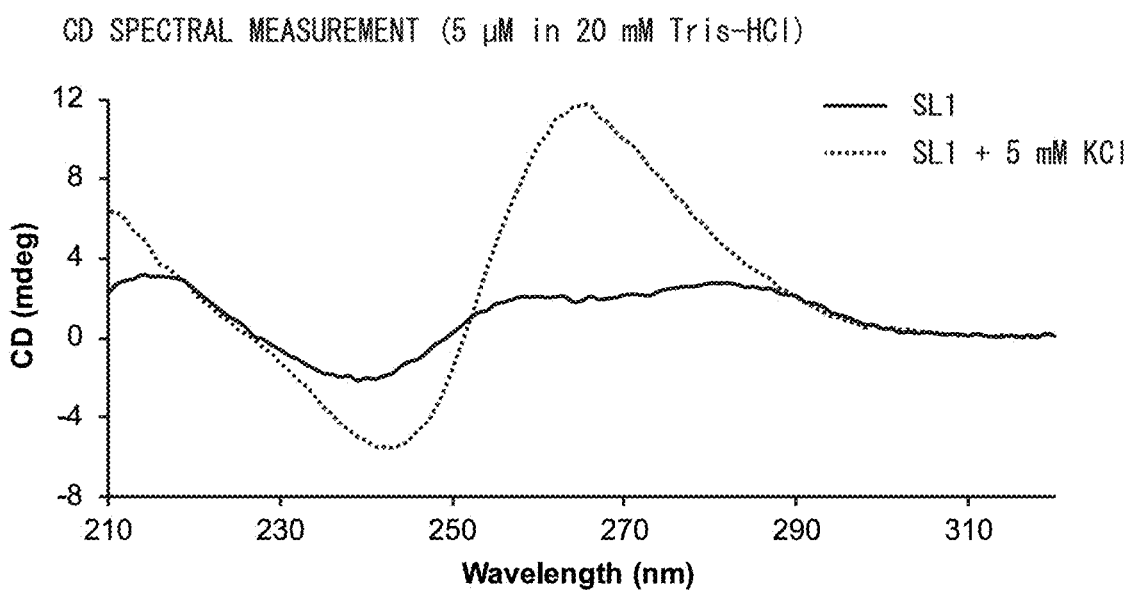
FIG. 11 is a diagram of the results showing the presence of a guanine quadruplex structure of SL1, obtained in Examples.
Figure 12:
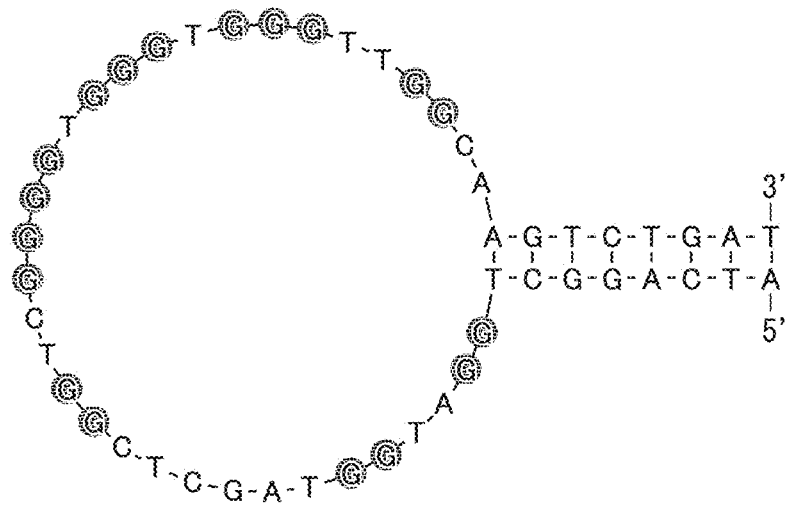
FIG. 12 is a schematic diagram showing a position of guanine in a loop region of SL1.

The results are shown in FIG. 11. In the system of SL1+5 mM KCl, a negative peak at around 245 nm and a positive peak at around 264 nm were detected. In the system of SL1 that does not contain KCl, a significant peak was not detected. Therefore, SL1 has been suggested to have a guanine quadruplex structure. The positions of guanine in the loop region of SL1 are shown in FIG. 12.

Figure 13:
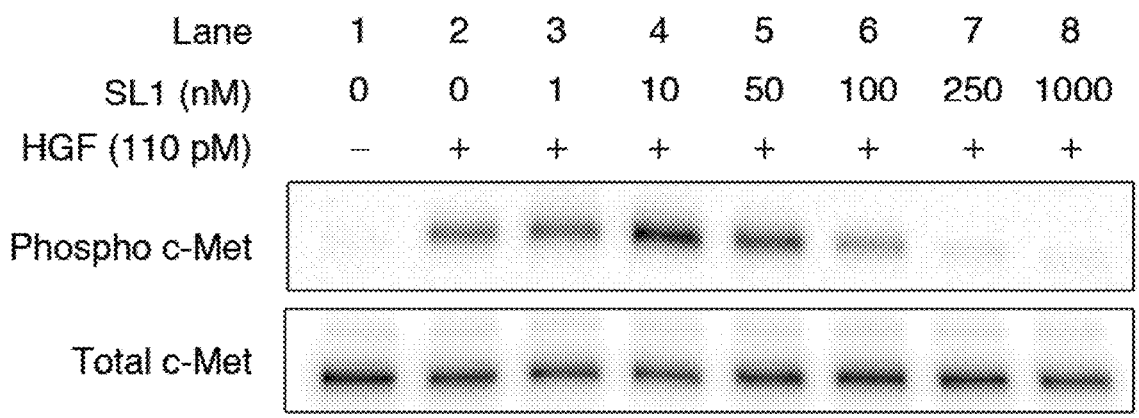
FIG. 13 is a diagram of the results showing inhibition of phosphorylation of c-Met by SL1, obtained in Examples.

Whether or not SL1 inhibits c-Met signaling was verified. A549 cells after 24-hour culture in a serum-free medium were immersed in a liquid containing HGF and SL1 at the following concentration and allowed to react for 15 minutes. As shown in FIG. 13, the concentration of HGF in the liquid was set to 110 pM, and the concentration of SL1 in the liquid was set to 0 nM, 1 nM, 10 nM, 50 nM, 100 nM, 250 nM, or 1000 nM. The A549 cell is a strain expressing c-Met (HGF receptor). The A549 cells after the reaction were solubilized and the resulting protein samples were analyzed by Western blotting. Phosphorylated c-Met (Phospho c-Met) was detected using a phosphorylated c-Met detection antibody (Phospho-Met (Tyr1234/1235) (D26) XP (registered trademark) Rabbit mAb #3077, available from Cell Signaling Technology Inc.) as a primary antibody of Western blotting. Hereinafter, the phosphorylation of c-Met was detected using an HRP-labeled secondary antibody (available from Dako Corporation, Rabbit Immunoglobulins P0448 peroxidase-labeled, affinity purification) that binds to the primary antibody.

The results are shown in FIG. 13. It has been confirmed that the signal indicating the presence of Phospho c-Met is decreased as the concentration of SL1 which has been brought into contact with A549 cells is increased. Therefore, SL1 has been shown to inhibit HGF-induced phosphorylation of c-Met.

Whether or not SL1 inhibits migration of cancer cells was verified.

SUIT-2 cells were cultured for 3 days to form colonies. Thereafter, the SUIT-2 cells were cultured into each of a system of cells cultured in a medium with no addition of HGF and SL1 (No treatment), a system of cells cultured in a medium with addition of 110 pM of HGF (+HGF), a system of cells cultured in a medium with addition of 110 pM of HGF and 1 μM of SL1 (+HGF, SL1), or a system of cells cultured in a medium with addition of 110 pM of HGF and 1 μM of SL1 reverse sequence (+HGF, SL1 Reverse), and the appearance of the cells was observed 18 hours after addition.

Figure 14:
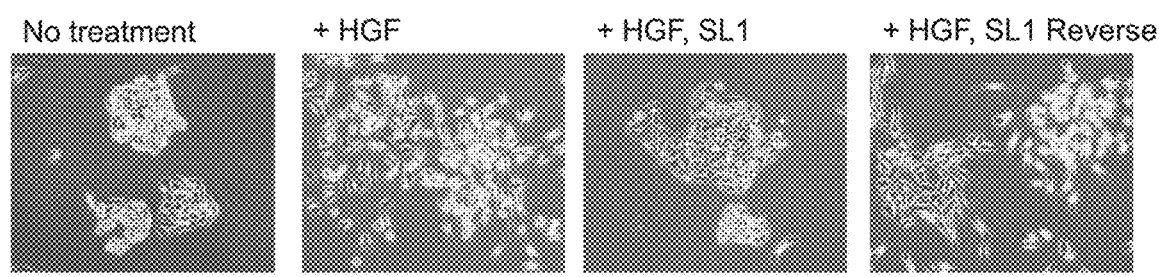
FIG. 14 is a diagram of the results showing inhibition of migration of cancer cells by SL1, obtained in Examples.

The results are shown in FIG. 14. Migration of cells was inhibited in the SUIT-2 cells to which HGF and SL1 were added, as compared with the SUIT-2 cells to which HGF was added and SL1 was not added. Therefore, it was demonstrated that migration of cancer cells can be inhibited by SL1.

(SL1 Dimer)

A polynucleotide consisting of the base sequence set forth in SEQ ID NO: 7, a polynucleotide consisting of the base sequence set forth in SEQ ID NO: 8, a polynucleotide consisting of the base sequence set forth in SEQ ID NO: 9, and a polynucleotide consisting of the base sequence set forth in SEQ ID NO: 10 were synthesized.

Figure 15:
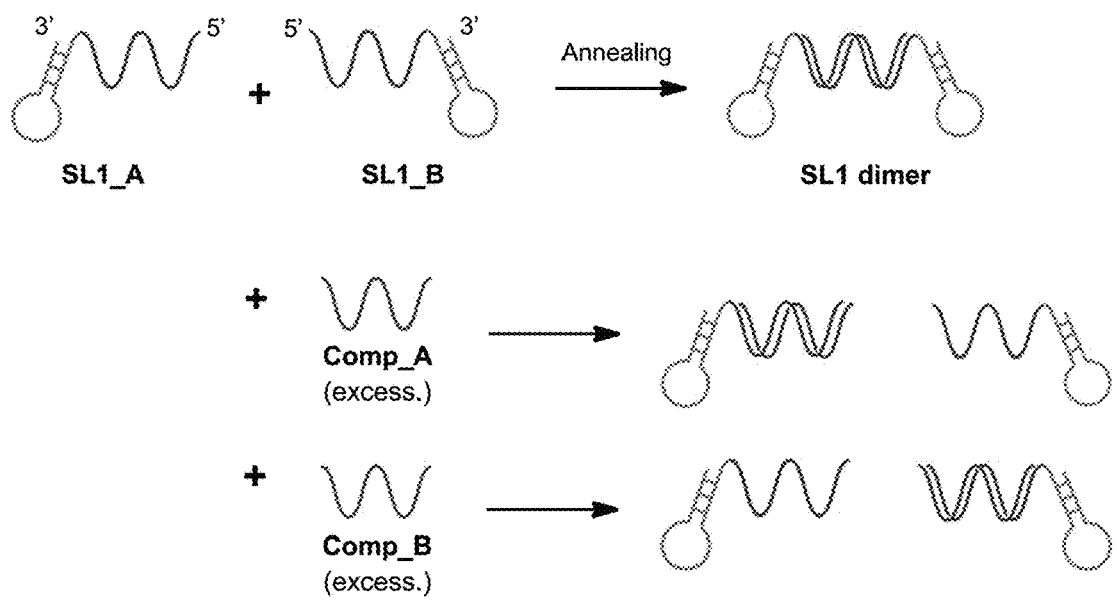
FIG. 15 is a schematic diagram showing the formation of an SL1 dimer prepared in Examples.

The polynucleotide according to SEQ ID NO: 7 forms SL1_A shown in FIG. 15.

The polynucleotide according to SEQ ID NO: 8 forms SL1_B shown in FIG. 15.

SL1_A is SL1 having a sequence for formation of a dimer added at the 5' terminal. Similarly, SL1_B is SL1 having a sequence for formation of a dimer added at the 5' terminal. The sequence at the 5' terminal of SL1_A and the sequence at the 5' terminal of SL1_B are sequences complementary to each other. By hybridization between the complementary sequences of SL1_A and SL1_B, an SL1 dimer is formed as shown in FIG. 15.

The polynucleotide according to SEQ ID NO: 9 forms Comp_A shown in FIG. 15.

The polynucleotide according to SEQ ID NO: 10 forms Comp_B shown in FIG. 15.

Comp_A is a polynucleotide consisting of a nucleic acid sequence identical to the sequence added at the 5' terminal of SL1_B for the formation of a dimer. Comp_B is a polynucleotide consisting of a nucleic acid sequence identical to the sequence added at the 5' terminal of SL1_A for the formation of a dimer.

As shown in FIG. 15, the formation of a dimer of SL1_A is inhibited by hybridization of Comp_A with SL1_A in place of SL1_B. In addition, the formation of a dimer of SL1_B is inhibited by hybridization of Comp_B with SL1_B in place of SL1_A.

Figure 16:
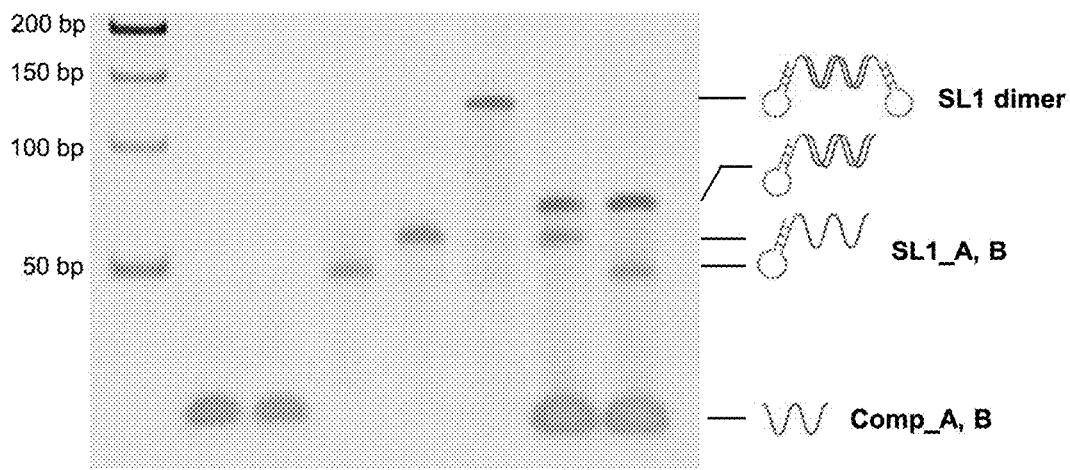
FIG. 16 is a diagram of the results showing the formation of an SL1 dimers or the like, obtained in Examples.

With respect to the presence or absence of the formulation of each polynucleotide of SL1_A, SL1_B, Comp_A, and Comp_B, according to seven sets of combinations shown in FIG. 16, reaction liquids of Dulbecco's Phosphate-Buffered Saline (DPBS) containing the corresponding polynucleotide were prepared. "+" in FIG. 16 indicates that the corresponding polynucleotide is formulated in the reaction liquid. "−" in FIG. 16 indicates that the corresponding polynucleotide is not formulated in the reaction liquid. Each reaction liquid was allowed to react at 95° C. for 5 minutes, cooled to 25° C. at a cooling rate of −0.1° C./sec, and subjected to Native PAGE on a 6% polyacrylamide gel.

The results are shown in FIG. 16. It was confirmed that an SL1 dimer was formed only in the reaction liquid containing SL1_A and SL1_B and not containing Comp_A and Comp_B.

Figure 17:
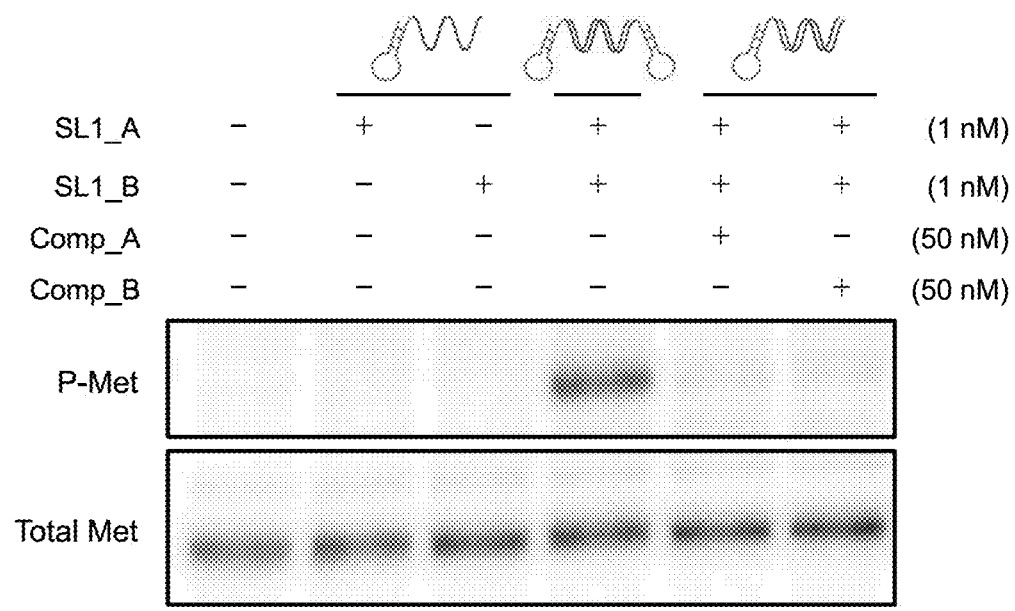
FIG. 17 is a diagram showing the results of induced activation of c-Met by an SL1 dimer, obtained in Examples.

After A549 cells were cultured in starvation conditions for 24 hours, with respect to the presence or absence of addition of each polynucleotide of SL1_A, SL1_B, Comp_A, and Comp_B, according to six sets of combinations shown in FIG. 17, the polynucleotide was added to the corresponding culture solution. "+" in FIG. 17 indicates that the corresponding polynucleotide is added into a medium. "−" in FIG. 17 indicates that the corresponding polynucleotide is not added into a medium. After the addition of polynucleotides, each medium was allowed to react for 15 minutes. The A549 cells after the reaction were solubilized and the resulting protein samples were subjected to Western blotting, thus detecting phosphorylated c-Met (P-Met).

The results are shown in FIG. 17. The phosphorylation of c-Met was confirmed only in the protein sample obtained from the cells cultured in a medium containing SL1_A and SL1_B and not containing Comp_A and Comp_B. Therefore, it has been demonstrated that the activation of c-Met was induced by formation of an SL1 dimer.

Whether or not the length of a linker connecting between SL1 dimers has an effect on activation of c-Met was examined.

A polynucleotide consisting of the base sequence set forth in SEQ ID NO: 11 was synthesized.

Figure 18:
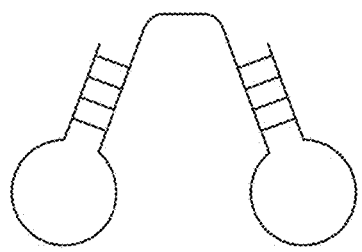
FIG. 18 is a schematic diagram showing an SL1 dimer prepared in Examples.

The polynucleotide according to SEQ ID NO: 11 forms an SL1 dimer_5 shown in FIG. 18.

The sequence of bases 1 to 50 and the sequence of bases 56 to 105 in the base sequence set forth in SEQ ID NO: 11 are sequences of the polynucleotide which forms the Stem-Loop1 (SL1). The sequence of bases 51 to 55 in the base sequence set forth in SEQ ID NO: 11 is a sequence of poly-dT where five T's are consecutive and forms a linker that connects SL1 dimers. Incidentally, the sequence of the stem structure of the first SL1 counted from the 5' terminal is different from the sequence of the stem structure of the second SL1.

Thus, the SL1 dimer_5 has a poly-dT of five bases connecting between two SL1's.

In addition to the L1 dimer_5, an SL1 dimer_20 in which the number of bases in poly-dT in the SL1 dimer_5 was changed from 5 to 20, and an SL1 dimer_40 in which the number of bases in poly-dT in the SL1 dimer_5 was changed from 5 to 40 were also respectively synthesized.

A549 cells after 24-hour culture in a serum-free medium were immersed in a liquid containing the SL1_dimer_5 at the following concentration and allowed to react for 15 minutes. The concentration of the SL1_dimer_5 in the liquid was set to 0 pM, 10 pM, 50 pM, 100 pM, 250 pM, 500 pM, or 1000 pM. The A549 cells after the reaction were solubilized and the resulting protein samples were analyzed by Western blotting to thereby detect phosphorylated c-Met (p-Met). Further, phosphorylated c-Met (p-Met) was analogously detected using the SL1_dimer_20 in place of the SL1_dimer_5. Phosphorylated c-Met (p-Met) was analogously detected using the SL1_dimer_40 in place of the SL1_dimer_5. Phosphorylated c-Met (p-Met) was analogously detected using HGF in place of the SL1_dimer_5.

Figure 19:
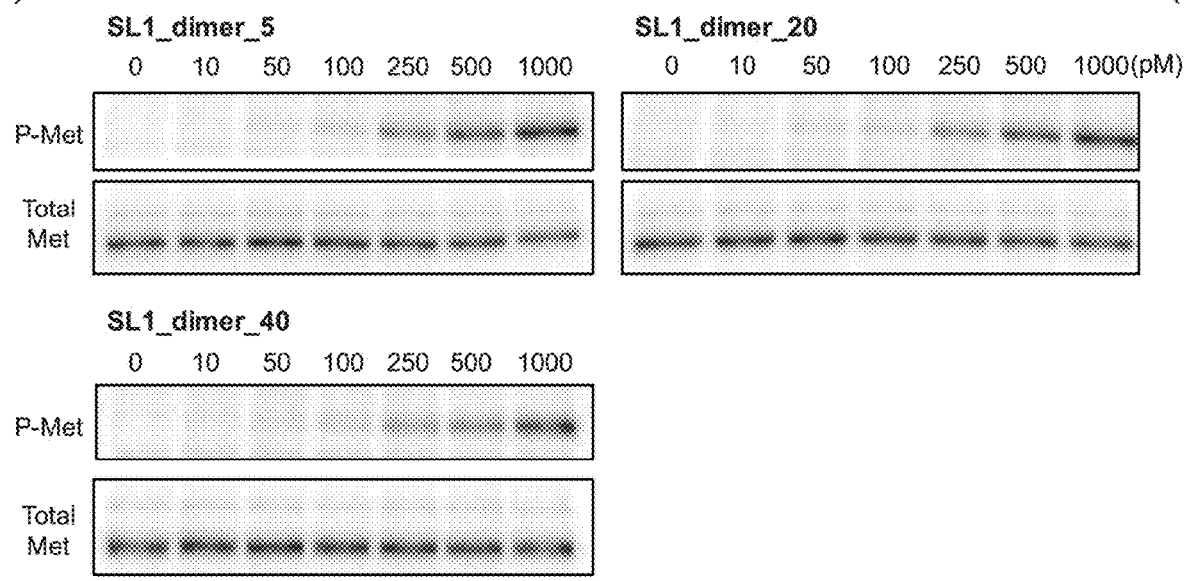
FIG. 19 is a diagram showing the results of phosphorylation of c-Met by an SL1 dimer, obtained in Examples.
Figure 20:
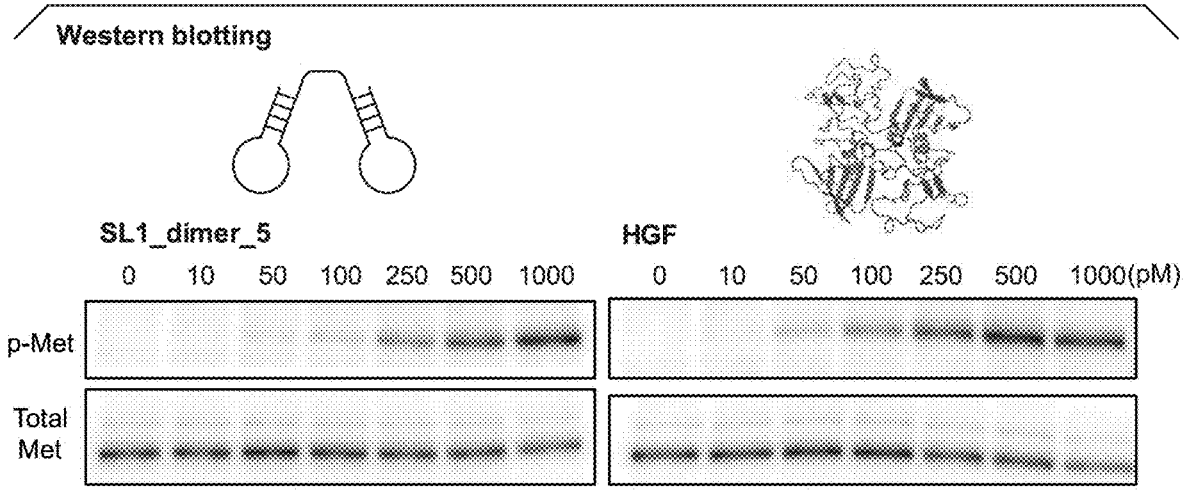
FIG. 20 is a diagram showing the results of phosphorylation of c-Met by an SL1 dimer, obtained in Examples.

The results are shown in FIGS. 19 and 20. According to Western blotting, all of SL1_dimer_5, SL1_dimer_20, and SL1_dimer_40 exhibited detection of p-Met in the case of being treated at a concentration of the SL1_dimer of 100 pM or more.

The effect of the length of a linker connecting between SL1 dimers on activation of c-Met was analyzed in more detail.

With respect to the SL1_A and SL1_B, ds-20 consisting of a polynucleotide of 20 bases was prepared as a sequence for the formation of a dimer at the 5' terminal. Similarly, ds30, ds40, and ds60 each consisting of a polynucleotide of 30 bases, 40 bases, and 60 bases were prepared as sequences for the formation of a dimer at the 5' terminal. ds refers to a double-stranded DNA.

An SL1 dimer_0 in which the number of bases in poly-dT in the SL1 dimer_5 was changed from 5 to 0 was prepared and designated as ss0. An SL1 dimer_10 in which the number of bases in poly-dT in the SL1 dimer_5 was changed from 5 to 10 was prepared and designated as ss10. The SL1 dimer_20 prepared above was used and designated as ss20. ss refers to a single-stranded DNA.

A549 cells were treated with each of ss0, ss10, ss20, ds20, ds30, ds40, and ds60 each at a concentration of 10 nM and subjected to an ELISA assay, thereby determining the relative value of the phosphorylation level.

Figure 21:
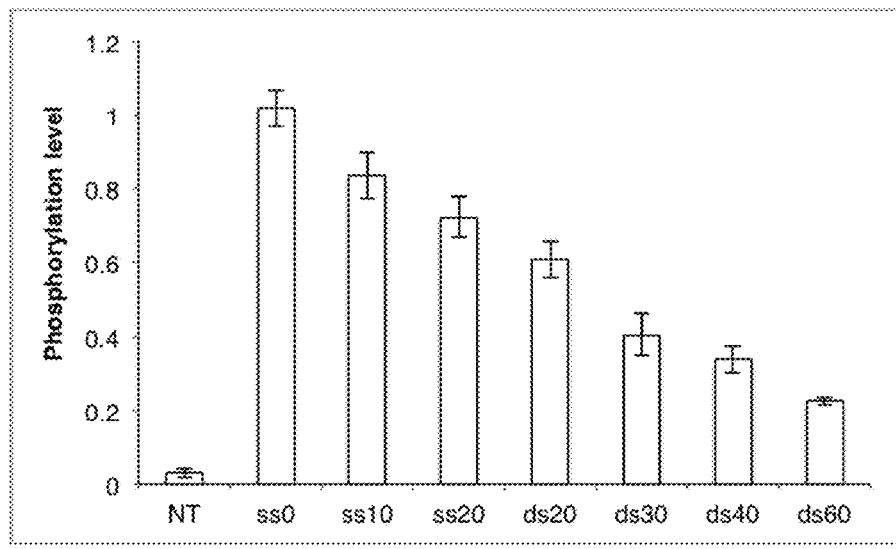
FIG. 21 is a graph showing the comparison results of effects of the length of a linker connecting between SL1 dimers on phosphorylation of c-Met, obtained in Examples.

The results are shown in FIG. 21. In FIG. 21, NT represents a negative control to which no ligand was added. As will be understood from the graph of FIG. 21, it was demonstrated that c-Met is activated as the linker length is shorter. In comparison of a single-stranded DNA linker and a double-stranded DNA linker each having the same length, the single-stranded DNA linker activated c-Met more effectively than the double-stranded DNA linker.

Whether or not an SL1 dimer_5 induces cell migration was verified.

DU145 cells were cultured for 3 days to form colonies. Thereafter, the DU145 cells were cultured into each of a system of cells cultured in a medium with no addition of HGF and SL1 dimer_5 (No treatment), a system of cells cultured in a medium with addition of 500 pM of HGF (+HGF), a system of cells cultured in a medium with addition of 500 pM of SL1 dimer_5 (+SL1 dimer_5), and a system of cells cultured in a medium in which SL1 of SL1 dimer_5 and a linker are disconnected and added (+Split dimer), and the appearance of the cells was observed 24 hours after addition.

Figure 22:
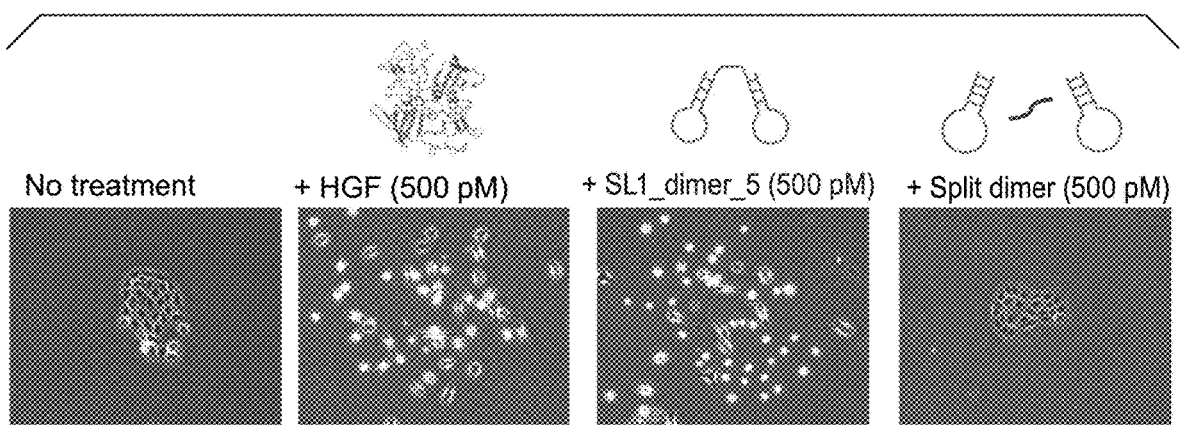
FIG. 22 is a diagram of the results showing promotion of migration of a cancer cell by an SL1 dimer, obtained in Examples.

The results are shown in FIG. 22. The migration of cells was observed in the DU145 cells to which the SL1 dimer_5 was added, similar to the DU145 cells to which HGF was added. Accordingly, it was demonstrated that migration of cells can be promoted by the SL1 dimer_5.

Whether or not an SL1 dimer promotes cell growth was verified.

Human umbilical vein endothelial cells (HUVECs) were cultured in a medium containing HGF, ss0, ss0 reverse sequence, or a solvent as a control for 6 days, and an increase in the number of cells was measured.

As compared to the case of being treated with a solvent as a control, HUVECs treated with 1 nM of HGF exhibited a cell growth promoting effect. HUVECs treated with 0.1 nM, 0.5 nM or 5 nM of ss0 also exhibited a concentration-dependent cell growth promoting effect, as compared to the case of being treated with a solvent as a control.

The sequence of SL1 was modified to thereby verify an effect on the binding to c-Met.

Figure 23:
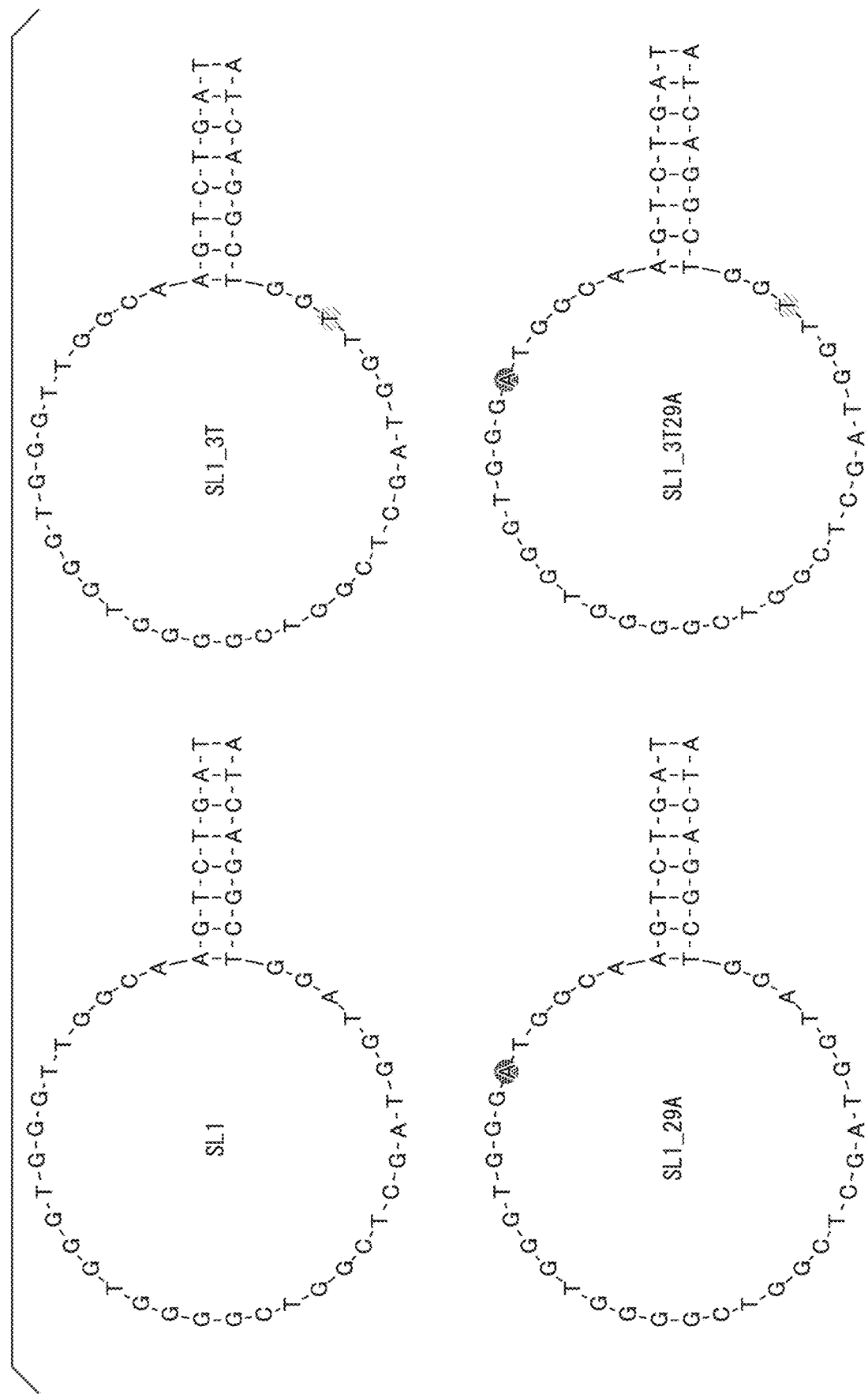
FIG. 23 is a schematic diagram of an SL1 mutant obtained in Examples.

FIG. 23 shows a schematic diagram of SL1 mutants. SL1_3T has a base sequence set forth in SEQ ID NO: 2, by changing into the sequence of a G-loop of SL1 set forth in SEQ ID NO: 1.

SL1_3T has a substitution of the $3^{rd}$ A to T in the base sequence set forth in SEQ ID NO: 1.

SL1_29A has a base sequence set forth in SEQ ID NO: 3, by changing into the sequence of a G-loop of SL1 set forth in SEQ ID NO: 1. SL1_29A has a substitution of the $29^{th}$ T to A in the base sequence set forth in SEQ ID NO: 1.

SL1_3T29A has abase sequence set forth in SEQ ID NO: 4, by changing into the sequence of a G-loop of SL1 set forth in SEQ ID NO: 1. SL1_3T29A has a substitution of the $3^{rd}$ A to T and a substitution of the $29^{th}$ T to A in the base sequence set forth in SEQ ID NO: 1.

For these SL1 SL1_3T, SL1_29A, and SL1_3T29A, a dimer whose linker is single-stranded ss-0 (0 base) was prepared.

A549 cells were cultured in starvation conditions for 24 hours, and 1 nM of each of SL1 dimer, SL1_3T dimer, SL1_29A dimer, SL1_3T29A dimer, or a solvent as a control was added thereto, followed by reaction at 37° C. The cells were solubilized and the resulting protein samples were subjected to an ELISA assay and a BCA assay, thereby measuring a phosphorylation level of c-Met.

Phosphorylation of c-Met had been promoted in the SL1_3T dimer, as compared to the SL1 dimer. Phosphorylation of c-Met had been promoted in the SL1_29A dimer at substantially the same level as in the SL1 dimer. In the SL1_3T29A dimer, c-Met had been phosphorylated at substantially the same level as in the SL1 dimer.

Individual configurations and combinations thereof in individual embodiments are of illustrative purposes only, and additions, omissions, substitutions, and other modifications of the configuration can be made without departing from the spirit of the present invention. The present invention is not limited to the foregoing embodiments, but rather, is only limited by the scope of the claims appended hereto.

REFERENCE SIGNS LIST 1, 2, 3 . . . aptamer, 4, 5, 6, 7, 8a, 8b . . . multi-structure aptamer, 10 . . . polynucleotide, 20 . . . loop structure, 30 . . . stem structure, 40 . . . linker, 100, 101 . . . aptamer-immobilized carrier, 110, 120 . . . solid phase carrier

---

What is claimed is:

1. An aptamer consisting of a polynucleotide of any of the following (a) to (c) and capable of binding to an HGF receptor to exhibit an activity of inhibiting the binding of HGF to the HGF receptor,
   (a) a polynucleotide consisting of a base sequence set forth in SEQ ID NO: 1,
   (b) a polynucleotide consisting of a base sequence having the deletion, substitution, insertion and/or addition of one to two bases in the base sequence set forth in SEQ ID NO: 1, and
   (c) a polynucleotide consisting of a base sequence having a sequence identity of 80% or more to the base sequence set forth in SEQ ID NO: 1.

2. The aptamer according to claim 1, wherein the aptamer has a loop structure.

3. The aptamer according to claim 2, wherein the aptamer further has a double-stranded stem structure connected to the loop structure.

4. The aptamer according to claim 2, wherein the loop structure consists of a polynucleotide chain having 28 to 40 bases.

5. The aptamer according to claim 1, wherein the polynucleotide of (a) to (c) forms a guanine quadruplex structure.

6. An agent for treating an HGF receptor signaling-related disease, comprising the aptamer according to claim 1 as an active ingredient.

7. A cell culture composition, comprising the aptamer according to claim 1 as an active ingredient.

8. A cell culture method, comprising culturing an HGF receptor-expressing cell in a medium containing the aptamer according to claim 1.

9. A method for inhibiting the binding of HGF to an HGF receptor, comprising bringing the aptamer according to claim 1 into contact with an HGF receptor-expressing cell.

* * * * *